(12) United States Patent
Borrell Bilbao et al.

(10) Patent No.: US 9,630,962 B2
(45) Date of Patent: Apr. 25, 2017

(54) 4-AMINO-6-(2,6-DICHLOROPHENYL)-2-(PHENYLAMINO)-PYRIDO[2,3-D]PYRIMIDIN-7(8H)-ONE DERIVATIVES, SYNTHESIS AND USES THEREOF

(71) Applicants: INSTITUT QUÍMIC DE SARRIÁ, CETS FUNDACIÓ PRIVADA, Barcelona (ES); HOSPITAL CLÍNIC DE BARCELONA, Barcelona (ES); FUNDACIÓ CLINIC PER A LA RECERCA BIOMÈDICA (FCRB), Barcelona (ES); INSTITUT D'INVESTIGACIONS BIOMÈDIQUES AUGUST PI I SUNYER, Barcelona (ES)

(72) Inventors: José Ignacio Borrell Bilbao, Barcelona (ES); Jordi Teixido Closa, Barcelona (ES); Raimon Puig De La Bellacasa Cazorla, Barcelona (ES); Dolors Colomer Pujol, Barcelona (ES); Gael Roue, Barcelona (ES); Patricia Pérez-Galán, Barcelona (ES)

(73) Assignees: HOSPITAL CLINIC DE BARCELONA, Barcelona (ES); FUNDACIÓ CLINIC PER A LA RECERCA BIOMÈDICA, Barcelona (ES); INSTITUT D'INVESTIGACIONS BIOMÈDIQUES AUGUST PI I SUNYER, Barcelona (ES); INSTITUT QUÍMIC DE SARRIÁ, CETS FUNDACIÓ PRIVADA, Barcelona (ES)

(*) Notice: Subject to any disclaimer, the term of this patent is extended or adjusted under 35 U.S.C. 154(b) by 0 days.

(21) Appl. No.: 14/897,590

(22) PCT Filed: Jun. 16, 2014

(86) PCT No.: PCT/EP2014/062563
§ 371 (c)(1),
(2) Date: Dec. 10, 2015

(87) PCT Pub. No.: WO2014/198960
PCT Pub. Date: Dec. 18, 2014

(65) Prior Publication Data
US 2016/0176866 A1 Jun. 23, 2016

(30) Foreign Application Priority Data
Jun. 14, 2013 (EP) .................... 13382225

(51) Int. Cl.
| | | |
|---|---|---|
| A61K 31/136 | (2006.01) |
| A61K 31/395 | (2006.01) |
| A61K 31/435 | (2006.01) |
| A61K 31/4353 | (2006.01) |
| A61K 31/4375 | (2006.01) |
| A61K 31/495 | (2006.01) |
| A61K 31/436 | (2006.01) |
| C07D 471/04 | (2006.01) |
| A61K 31/496 | (2006.01) |

(52) U.S. Cl.
CPC .......... *C07D 471/04* (2013.01); *A61K 31/136* (2013.01); *A61K 31/395* (2013.01); *A61K 31/435* (2013.01); *A61K 31/4353* (2013.01); *A61K 31/4375* (2013.01); *A61K 31/495* (2013.01); *A61K 31/496* (2013.01)

(58) Field of Classification Search
CPC .. A61K 31/136; A61K 31/395; A61K 31/435; A61K 31/4353; A61K 31/4375; A61K 31/495; A61K 31/496
See application file for complete search history.

(56) References Cited

U.S. PATENT DOCUMENTS

| | | |
|---|---|---|
| 3,702,889 A | 11/1972 | Goldman |
| 2009/0062274 A1 | 3/2009 | Baik et al. |
| 2009/0312321 A1 | 12/2009 | Ren et al. |
| 2013/0116262 A1 | 5/2013 | Crawford et al. |

FOREIGN PATENT DOCUMENTS

| | | |
|---|---|---|
| WO | 2004063195 A1 | 7/2004 |
| WO | 2012028756 A1 | 3/2012 |

OTHER PUBLICATIONS

Advani, R., et al., "The BTK Inhibitor PCI-32765 is highly active and well tolerated in patients (PTS) with relapsed/refractory B cell malignancies: final results from a phase I study", "Annals of Oncology", Jun. 2011, p. iv136 (Abstract 153), vol. 22 Supplement 4.

Al-Ameri, A., et al., "Phase II Study of Dasatinib in Patients with Relapsed Chronic Lymphocytic Leukemia", "Blood (ASH Annual Meeting Abstracts)", Nov. 19, 2010, pp. 1-2 (Abstract 4488), vol. 116, No. 21.

Amrein, P., et al., "Phase II Study of Dasatinib in Relapsed or Refractory Chronic Lymphocytic Leukemia", "Clin Cancer Res", Mar. 14, 2011, pp. 2977-2986, vol. 17.

(Continued)

*Primary Examiner* — Yong Chong
(74) *Attorney, Agent, or Firm* — Hultquist, PLLC; Steven J. Hultquist

(57) ABSTRACT

The present invention is related to 4-amino-6-(2,6-dichlorophenyl)-2-(phenylamino)-pyrido[2,3-d]pyrimidin-7(8H)-one derivatives, to the preparation of such compounds, to pharmaceutical compositions comprising them, and to their use in the treatment and/or prevention of a non-Hodgkin's lymphoma.

9 Claims, 3 Drawing Sheets

(56) References Cited

OTHER PUBLICATIONS

Antczak, C., et al., "Structure-activity relationships of 6-(2,6-dichlorophenyl)-8-methyl-2-(phenylamino)pyrido[2,3-d] pyrimidin-7-ones: Toward selective Abl inhipitors", "Bioorganic & Medicinal Chemistry Letters", Oct. 23, 2009, pp. 6872-6876, vol. 19.

Attenburrow, J., et al., "194. A synthesis of vitamin a from cyclohexanone", "Journal of the Chemical Society (Resumed)", 1952, pp. 1094-1111.

Byrd, J., et al., "The Bruton's Tyrosine Kinase (BTK) Inhibitor Ibrutinib (PCI-32765) Promotes High Response Rate, Durable Remissions, and Is Tolerable in Treatment Na.Ive (TN) and Relapsed or Refractory (RR) Chronic Lymphocytic Leukemia (CLL) or Small Lymphocytic Lymphoma (SLL) Patients Including Patients with High-Risk (HR) Disease: New and Updated Results of 116 Patients in a Phase Ib/II Study", "Blood", Nov. 16, 2012, pp. 14 (Abstract 189), vol. 120, No. 21.

Filipski, K., et al, "A versatile copper-catalyzed coupling reaction of pyridin-2(1H)-ones with aryl halides", "Tetrahedron Letters", Sep. 18, 2006, pp. 7677-7680, vol. 47.

Fowler, N., et al., "The Bruton's Tyrosine Kinase Inhibitor Ibrutinib (PCI-32765) Is Active and Tolerated in Relapsed Follicular Lymphoma", "Blood (ASH Annual Meeting Abstracts)", Nov. 16, 2012, pp. 12 (Abstract 156), vol. 120, No. 21.

Friedberg, J., et al., "Inhibition of Syk with fostamatinib disodium has significant clinical activity in non-Hodgkin lymphoma and chronic lymphocytic leukemia", "Blood", Nov. 17, 2009, pp. 2578-2585, vol. 115, No. 13.

Galve, I., et al., "Synthesis of 2-arylamino substituted 5,6-dihydropyrido[2,3-d]pyrimidine-7 (8H)-ones from arylguanidines", "Molecular Diversity", Nov. 2012, pp. 639-649, vol. 16, No. 4.

Herman, S., et al., "F ostamatinib inhibits B-cell receptor signaling, cellular activation and tumor proliferation in patients with relapsed and refractory chronic lymphocytic leukemia", "Leukemia", Mar. 1, 2013, pp. 1-4.

Hoellenriegel, J., et al., "Selective, novel spleen tyrosine kinase (Syk) inhibitors suppress chronic lymphocytic leukemia B-cell activation and migration", "Leukemia", Feb. 24, 2012, pp. 1576-1583, vol. 26.

Iversen, P., et al., "A Comparison of Assay Performance Measures in Screening Assays: Signal Window, Z' Factor, and Assay Variability Ratio", "Journal ofBiomolecular Screening", Apr. 2006, pp. 247-252, vol. 11, No. 3.

Jares, P., et al., "Molecular pathogenesis of mantle cell lymphoma", "TheJoumalofClinicalInvestigation", Oct. 2012, pp. 3416-3423, vol. 122, No. 10.

Kim, J., et al., "Ammonium salts as an inexpensive and convenient nitrogen source in the Cu-catalyzed amination of aryl halides at room temperature", "Chem. Commun.", May 23, 2008, pp. 3052-3054.

Klutchko, S., et al., "2-Substituted Aminopyrido [2,3-d]pyrimidin-7 (8H)-ones. Structure-Activity Relationships Against Selected Tyrosine Kinases and in Vitro and in Vivo Anticancer Activity", "J. Med. Chem.", Aug. 13, 1998, pp. 3276-3292, vol. 41.

Kridel, R., et al., "Pathogenesis of follicular lymphoma", "The Journal of Clinical Investigation", Oct. 2012, pp. 3424-3431, vol. 122, No. 10.

Lopez-Guerra, M., et al., "Sorafenib targets BCR kinases and blocks migratory and microenvironmental survival signals in CLL cells", "Leukemia", Dec. 20, 2011, pp. 1429-1432, vol. 26.

Lou, Y., et al., "Bruton's Tyrosine Kinase Inhibitors: Approaches to Potent and Selective Inhibition, Preclinical and Clinical Evaluation for Inflammatory Diseases and B Cell Malignancies", "Journal of Medicinal Chemistry", Mar. 6, 2012, pp. 4539-4550, vol. 55.

McCraig, A., et al., "Dasatinib inhibits B cell receptor signalling in chronic lymphocytic leukaemia but novel combination approaches are required to overcome additional pro-survival microenvironmental signals", "British Journal of Haematology", Feb. 24, 2011, pp. 1999-211, vol. 153.

Nogai, H., et al., "Pathogenesis of Non-Hodgkin's Lymphoma", "Journal of Clinical Oncology", Apr. 11, 2011, pp. 1803-1811, vol. 29, No. 14.

O'Brien, S., et al., "The Bruton's Tyrosine Kinase (BTK) Inhibitor PCI-32765 Induces Durable Responses in Relapsed or Refractory (RIR) Chronic Lymphocytic Leukemia/Small Lymphocytic Lymphoma (CLL/SLL): Follow-up of a Phase Ib/II Study", "Blood (ASH Annual Meeting Abstracts)", Nov. 18, 2011, pp. 12 (Abstract 983), vol. 118, No. 21.

Perez-Pi, I., et al., "Dehydrogenation of 5,6-Dihydropyrido(2,3-d)Pyrimidin-7(8H)-Ones: A Convenient Last Step for a Synthesis of Pyrido[2,3-d]Pyrimidin-7(8H)-Ones", "Heterocycles", Jun. 16, 2010, pp. 581-591, vol. 82, No. 1.

Robak, T., et al., "Tyrosine kinase inhibitors as potential drugs for 8-cell lymphoid malignancies and autoimmune disorders", "Expert Opin Investig Drugs.", May 22, 2012, pp. 921-947 (Abstract), vol. 21, No. 7.

Tilly, H., et al., "Diffuse large B-cell non-Hodgkin's lymphoma: ESMO Clinical Practice Guidelines for diagnosis, treatment and follow-up", "Annals of Oncology", May 2010, pp. v172-v174, vol. 21 (Supplement 5).

Victory, P., et al., "Nueva sintesis de pirido[2,3-d]pirimidinas. V. Deshidrogenacion del anillo dihidropiridonico en sistemas 5- o 6-alquil sustituidos", "AFINIDAD", Mar. 1989, pp. 107-113, vol. 46.

Wang, M., et al., "Interim Results of an International, Multicenter, Phase 2 Study of Bruton's Tyrosine Kinase (BTK) Inhibitor, Ibrutinib (PCI-32765), in Relapsed or Refractory Mantle Cell Lymphoma (MCL): Durable Efficacy and Tolerability with Longer Follow-up", "Blood", Nov. 16, 2012, pp. 1-2 (Abstract 904), vol. 120, No. 21.

Wilson, W., et al., "The Bruton's Tyrosine Kinase (BTK) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase 2 Study", "Blood (ASH Annual Meeting Abstracts)", Nov. 16, 2012, pp. 1-2 (Abstract 686), vol. 120, No. 21.

Zenz, T., et al., "From pathogenesis to treatment of chronic lymphocytic leukaemia", "Nature Reviews Cancer", Jan. 2010, pp. 37-50, vol. 10.

Zhang, J., et al., "A Simple Statistical Parameter for Use in Evaluation and Validation of High Throughput Screening Assays", "Journal of Biomolecular Screening", 1999, pp. 67-73, vol. 4, No. 2.

4-AMINO-6-(2,6-DICHLOROPHENYL)-2-(PHENYLAMINO)-PYRIDO[2,3-D]PYRIMIDIN-7(8H)-ONE DERIVATIVES, SYNTHESIS AND USES THEREOF

CROSS-REFERENCE TO RELATED APPLICATIONS

This application is a U.S. national phase under the provisions of 35 U.S.C. §371 of International Patent Application No. PCT/EP14/62563 filed Jun. 16, 2014, which in turn claims priority of European Patent Application No. 13382225.4 filed Jun. 14, 2013. The disclosures of such international patent application and European priority patent application are hereby incorporated herein by reference in their respective entireties, for all purposes.

FIELD OF THE INVENTION

The present invention relates to 4-amino-6-(2,6-dichlorophenyl)-2-(phenylamino)-pyrido[2,3-d]pyrimidin-7(8H)-one derivatives, to their preparation, to pharmaceutical compositions comprising them, and to their use in the treatment and/or prevention of non-Hodgkin's lymphomas.

BACKGROUND OF THE INVENTION

Non-Hodgkin's lymphomas (NHLs) represent a heterogeneous group of malignancies arising from the lymphoid system. They represent the malignant counterpart of different steps of B-lymphocyte differentiation. Similar to other types of cancer, they are the result of a multistep accumulation of genetic aberrations that induce a selective growth advantage of the malignant clone [Nogai H, Dorken B, Lenz G. Pathogenesis of non-Hodgkin's lymphoma. *J. Clin. Oncol.* 2011; 29(14), 1803-1811]. The World Health Organization classifies NHLs in three main groups: a) mature B cell neoplasms, b) mature T cell and natural killer (NK) cell neoplasms and c) immunodeficiency-associated lymphoproliferative disorders. Among the mature B cell neoplasms, chronic lymphocytic leukemia, mantle cell lymphoma, follicular lymphoma and diffuse large B cell lymphoma represent the four most relevant ones.

Chronic lymphocytic leukemia (CLL) is one of the most frequent tumors in Western countries. CLL represents 35% of all leukemias with an incidence of 3-7 per 100.000 habitants and reaches 12-15/100.000 in people over 60 years. The disease is clinically heterogeneous; some patients have a long clinical evolution with a stable disease, whereas others follow a progressive course with a median survival of 5-8 years. This heterogeneity is due to the existence of two major molecular groups, characterized respectively by the presence or absence of somatic mutations in the immunoglobulin genes. Different genetic alterations have been identified associated with particular clinical presentations and evolution. There is also evidence of genetic predisposition, but the initiating genetic alterations are largely unknown in both sporadic and inherited cases, and the somatic genetic basis of CLL remains largely unknown [Zenz T, Mertens D, Kuppers R, et al. From pathogenesis to treatment of chronic lymphocytic leukaemia. *Nat. Rev. Cancer* 2010; 10(1), 37-50]. Current treatments for the disease include chemotherapy, such as treatment with alkylating agents (chlorambucil, cyclophosphamide, bendamustine), purine analogs (fludarabine) and immunotherapeutic agents (rituximab and alemtuzumab), or the combination of immuno- and chemotherapy (the gold standard for CLL treatment is now fludarabine, cyclophosphamide and rituximab). However, none of these treatments are curative.

Mantle cell lymphoma (MCL) accounts for 5% to 10% of all lymphoma cases in adults. The overall incidence of MCL per 100.000 habitants is 0.55, increasing with age: 0.07 in patients aged <50 years, 2.97 in patients aged 70 to 79 years, and 2.78 in those aged > or =80 years. MCL is a B-cell neoplasia genetically characterized by the t(11;14)(q13;q32) translocation and the overexpression of its target gene cyclin D1. This tumor is considered one of the most aggressive lymphoid neoplasias and most patients follow a relative rapid evolution with limited responses to the current therapeutic strategies [Jares P, Colomer D, Campo E. Molecular pathogenesis of mantle cell lymphoma. *J. Clin. Invest.* 2012, 1; 122(10), 3416-23]. The current therapeutic strategies for the treatment of MCL are based on the use of combination chemotherapy with rituximab or more recently the use of bendamustine plus rituximab. In the last six years, two new drugs for relapsed or refractory MCL have been approved: the proteasome inhibitor bortezomib (approved by the US FDA) and the mTOR inhibitor temsirolimus (approved by the European Medicines Agency). Patients afflicted with MCL suffer from frequent relapses and they progressively develop resistance to treatment, emphasizing the need for new approaches. Currently, transplantation of hematopoietic progenitors (THP) is the only curative regimen, but it is not doable in the commonly aged patients affected from this lymphoma.

Follicular lymphoma (FL) is the most frequent low-grade NHL and accounts for approximately 20% of all malignant lymphomas with approximately 3 to 5 per 100.000 habitants and increases with age, with the median age at diagnosis being 60 years. The clinical course of FL can be highly variable, with overall survival rates ranging from only a few to more than 20 years. FL is derived from a germinal center B cell and is characterized by the presence of t(14;18)(q32; q21) translocation that juxtaposes the BCL2 gene and the IGH locus, leading to the overexpression of the antiapoptotic protein BCL2 [Kridel R, Sehn L H, Gascoyne R D. Pathogenesis of follicular lymphoma. *J. Clin. Invest.* 2012, 122(10), 3424-3431]. Most of FL patients show complete or partial responses with immunotherapy treatment. However, relapses are warranted in most of the cases making this disease incurable.

Diffuse large B-cell non-Hodgkin's lymphoma (DLBCL) constitutes 30%-58% of non-Hodgkin's lymphoma series representing the most frequent lymphoma. The crude incidence in the European Union is 3-4/100,000 per year and increases with age from 0.3/100,000/year (35-39 years) to 26.6/100,000/year (80-84 years) [H. Tilly, M. Dreyling (On behalf of the ESMO Guidelines Working Group). Diffuse large B-cell non-Hodgkin's lymphoma: ESMO Clinical Practice Guidelines for diagnosis, treatment and follow-up. *Ann. Oncol.* 2010; 21(suppl 5): v172-v174].

Treatment strategies of FL and DLBCL should be stratified according to age and the Follicular Lymphoma International Prognosis Index (FLIPI) or International Prognosis Index (IPI) that allows the feasibility of dose-intensified approaches based on patient's health report. Most of the treatments are based on the use of combination chemotherapy (mainly cyclophosphamide, doxorubicin, vincristine and prednisone (CHOP)) combined with rituximab. Lately, maintenance therapy with rituximab seems to delay the common relapses seen in these lymphomas.

The literature has reported that the most upstream tyrosine kinases LYN, SYK (spleen tyrosine kinase), and BTK (Bruton's tyrosine kinase) in the B-Cell Receptor (BCR) pathway are involved in NHLs, in particular in mature B cell neoplasms.

Dasatinib is an oral multikinase inhibitor targeting SRC and ABL kinases that is approved for treatment of chronic myeloid leukemia. Dasatinib has also been shown to inhibit LYN and BTK at low nanomolar concentrations. In vitro, dasatinib induces variable degrees of apoptosis in CLL cells [McCaig A M, Cosimo E, Leach M T, Michie A M. Dasatinib inhibits B cell receptor signalling in chronic lymphocytic leukaemia but novel combination approaches are required to overcome additional pro-survival microenvironmental signals. *Br. J. Haematol.* 2011, 153(2), 199-211; and López-Guerra M, Xargay-Torrent S, Pérez-Galán P, Saborit-Villarroya I, Rosich L, Villamor N, Aymerich M, Roué G, Campo E, Montserrat E, Colomer D. Sorafenib targets BCR kinases and blocks migratory and microenvironmental survival signals in CLL cells. *Leukemia.* 2012, 2 6(6), 1429-32]. Dasatinib as a single agent has activity in relapsed and refractory CLL. (Amrien et al, Amrein P C, Attar E C, Takvorian T, et al. Phase II study of dasatinib in relapsed or refractory chronic lymphocytic leukemia. Clin Cancer Res 2011; 17:2977-86; Al-Ameri A M, Badoux X, Ferrajoli A, et al. Phase II study of dasatinib in patients with relapsed chronic lymphocytic leukemia. Blood 2010; 116:4488). Dasatinib has been evaluated in CLL in combination with other drugs including rituximab, lenalidomide and bendamustine. In summary, it seems that dasatinib is an effective part of CLL treatment, particularly in the reduction of nodular tumor masses, but seems to have week efficacy on peripheral lymphocytes (Robak T, Robak E. Tyrosine kinase inhibitors as potential drugs for B-cell lymphoid malignancies and autoimmune disorders. Expert Opin Investig Drugs. 2012 July; 21(7):921-47).

The first clinical trial of a SYK inhibitor in a non-Hodgkin's lymphoma used fostamatinib in a phase 1/2 study in patients with relapsed/refractory non-Hodgkin's lymphoma and CLL [Friedberg J W, Sharman J, Sweetenham J, et al. Inhibition of Syk with fostamatinib disodium has significant clinical activity in non-Hodgkin's lymphoma and chronic lymphocytic leukemia. *Blood* 2010; 115(13):2578-2585]. The dose-limiting toxicity was a combination of diarrhea, neutropenia, and thrombocytopenia. In the phase 2 portion of the trial, the most common adverse events were reversible cytopenias, fatigue, diarrhea, and hypertension. Of 11 patients with CLL, 6 (55%) achieved a partial response (PR). The response rate in CLL was the highest, ahead of DLBCL (22%), MCL (11%), and FL (10%). Moreover, analysis of CLL patient material enrolled in this phase 1/2 study was used to evaluate the effects of fostamatinib on CLL cells in vivo after one cycle of treatment. This analysis demonstrated that Fostamatinib inhibits BCR signaling, cellular activation and tumor proliferation in vivo, in patients with relapsed and refractory chronic lymphocytic leukemia (S E M Herman et al Leukemia epub 1 Mar. 2013).

Newer more potent and more specific SYK inhibitors are in development [Hoellenriegel J, Coffey G P, Sinha U, et al. Selective, novel spleen tyrosine kinase (Syk) inhibitors suppress chronic lymphocytic leukemia B-cell activation and migration. *Leukemia* 2012, 26(7):1576-1583].

Ibrutinib is a BTK inhibitor, whose initial phase 1 dose escalation study reported responses in 60% of patients with various B-cell malignancies. In the 14 patients with CLL, the overall response (OR) was 79%, including 2 complete responses (CR). [Advani R H, Sharman J P, Smith S M, et al. The BTK inhibitor PCI-32765 is highly active and well tolerated in patients with relapsed/refractory B-cell malignancies: final results from a Phase I study. *Ann. Oncol.* 2011. Abstract 153]. A phase 1b/2 study of ibrutinib in CLL enrolled 2 cohorts: treatment-naive patients >65 years and relapsed/refractory patients. In the latter cohort, best responses were PR in 66% and complete responses in 1 of 61 patients studied, with no difference between dose levels [O'Brien S, Burger J A, Blum K A, et al. The Bruton's tyrosine kinase (BTK) inhibitor PCI-32765 induces durable responses in relapsed or refractory (R/R) chronic lymphocytic leukemia/small lymphocytic lymphoma (CLL/SLL): follow-up of a Phase Ib/II study. Blood (ASH Annual Meeting Abstracts) 2011, 118(21), 983]. Ibrutinib was well tolerated, and the most common side effects were diarrhea, nausea, fatigue, echymosis, upper respiratory tract infections, muscle spasms, arthralgia, peripheral edema, and pyrexia. The follow up of this study in 2012 further confirmed that ibrutinib was active in the treatment of naive patients (overall response (OR) of 71%, with complete response (CR) of 10% and partial response (PR) of 61%), relapsed/refractory patients (OR 67% with CR 3%, PR 64%), and high risk patients (OR 50% with CR 0%, PR 50%), with an estimated overall survival (OS) of 22 month in 96% of treated naive patients and 76% of relapsed/refractory and high risk patients (Byrd J, Blood 2012 120:21 Abstract 189)

In a phase 1 clinical trial in relapsed follicular lymphoma, ibrutinib was well tolerated and showed significant activity, allowing an OR of 54.5% (27% CR and 27% PR) and a duration of response that reached 12.3 months (Fowler N H, Blood 2012 120: 21 Abstract 156). In a phase 2 study in relapsed/refractory DLBCL, Ibrutinib was well tolerated, with OR of 21.7% (5% CR and 16.7% PR) (Wilson W H, Blood 2012 120:21 Abstract 686.). Finally, impressive results were obtained in a multicenter, phase 2 Study of Ibrutinib, in relapsed or refractory MCL with an OR of 66.1% (19.3% CR and 46.8% PR)(Wang, M, Blood 2012 120:21 Abstract 904).

From the previous discussion it becomes evident that there still is a non-satisfied need for clinically effective agents for the treatment of mature B cell neoplasms, more particularly for the treatment of CLL, MCL, FL and DLBCL and that targeting one or more of LYN, SYK, and BTK kinases with small molecular inhibitors seems to be a promising strategy in the treatment of these mature B cell neoplasms (CLL, MCL, FL and DLBCL).

The inventors have surprisingly found that 4-amino-6-(2, 6-dichlorophenyl)-2-(phenylamino)-pyrido[2,3-d]pyrimidin-7(8H)-one derivatives of formula (I) are capable of inhibiting one or more of BCR-related kinases (LYN, SYK, and/or BTK) kinases, arresting the growth of NHL cell lines. In addition, these compounds show low toxicity values in vitro. This discovery makes these compounds promising candidates for the treatment of non-Hodgkin's lymphomas, in particular for the treatment of mature B cell neoplasm, more particularly for the treatment of CLL, MCL, FL and DLBCL. The inventors have also discovered a process for obtaining these 4-amino-6-(2,6-dichlorophenyl)-2-(phenylamino)-pyrido[2,3-d]pyrimidin-7(8H)-one derivatives.

DESCRIPTION OF THE INVENTION

Definitions

Figure 1:
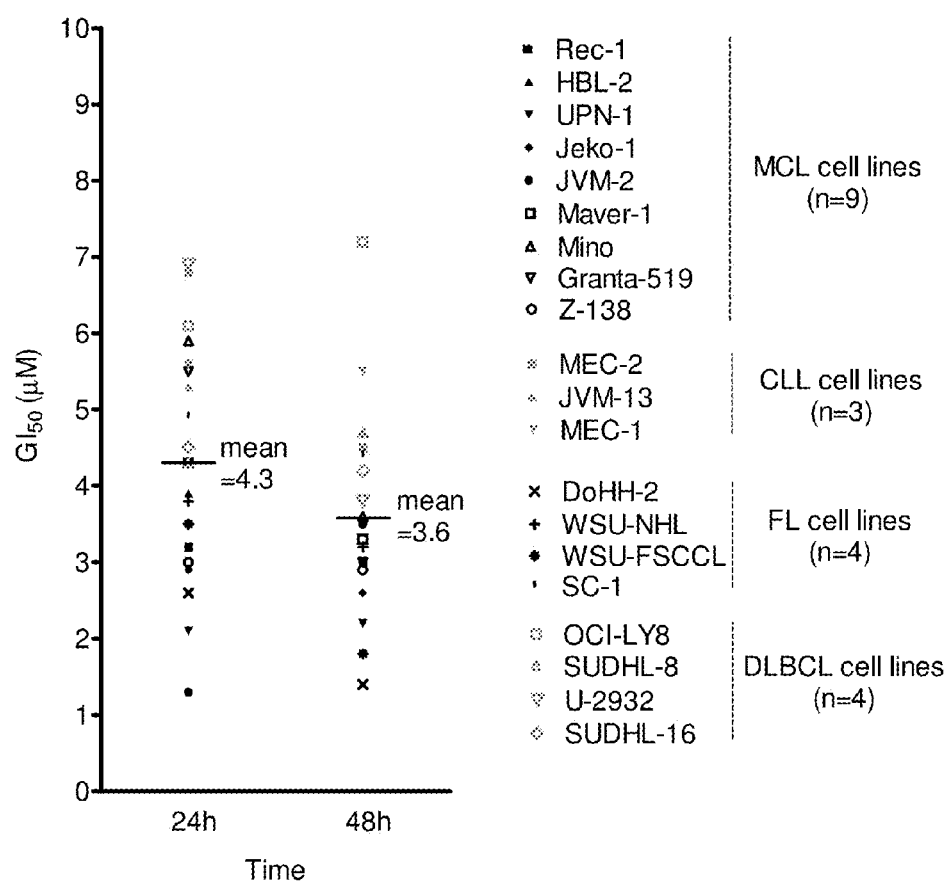
FIG. 1 illustrates the growth inhibitory effect of 4-amino-6-(2,6-dichlorophenyl)-8-methyl-2-(4-(4-methyl piperazin-1yl)phenylamino)pyrido[2,3-]pyrimidin-7(8H)-one) evaluated by MTT assay at 24 h and 48 h in MCL, CLL, FL and DLBCL cell lines. $GI_{50}$ doses are shown for each cell line.

The term "alkyl" as employed herein alone or as part of another group designates a linear or branched saturated monovalent hydrocarbon chain containing from of one to six carbon atoms, preferably from one to three carbon atoms. Examples of alkyls are methyl, ethyl, propyl, 2-propyl, n-butyl, isobutyl, sec-butyl, tert-butyl, n-pentyl, isopentyl, sec-pentyl, tert-pentyl, neopentyl, and the like.

The term "alkylene" as employed herein alone or as part of another group designates a linear or branched saturated divalent hydrocarbon chain containing from of one to six carbon atoms, preferably from one to three carbon atoms. Examples of alkylene are methylene (—$CH_2$—), ethylene (—$CH_2CH_2$—), trimethylene (—$CH_2CH_2CH_2$—) or tetramethylene (—$CH_2CH_2CH_2CH_2$—), methylethylene, (—$CH(CH_3)CH_2$—), pentamethylene (—$CH_2CH_2CH_2CH_2CH_2$—), hexamethylene (—$CH_2CH_2CH_2CH_2CH_2CH_2$—) and the like.

The term "alkoxy" as employed herein alone or as a part of another group designates an alkyl group as defined above linked through oxygen, i.e. —O-alkyl, wherein the alkyl group may be substituted by an aryl group as defined below. Examples of which include methoxy, ethoxy, isopropoxy, tertbutoxy, benzyloxy, and the like.

The term "alkoxyalkyleneoxy" refers to a —O-alkylene-O-alkyl group, wherein alkyl and alkylene are as defined above. Examples of alkoxyalkyleneoxy are methoxymethoxy, ethoxymethoxy, isopropoxymethoxy, tertbutoxymethoxy, methoxyethoxy, ethoxyethoxy, isopropoxyethoxy, tertbutoxyethoxy and the like.

The term "alkoxycarbonyl" refers to a —C(O)O-alkyl group, wherein alkyl is as defined above. Examples of alkoxycarbonyl are methoxycarbonyl, ethoxycarbonyl, isopropoxycarbonyl, tertbutoxycarbonyl and the like.

The term "alkylamino" refers to a —NHalkyl group, wherein alkyl is as defined above. Examples of alkylamino are methylamino, ethylamino, isopropylamino, tertbutylamino and the like.

The term "alkylcarbonyl" refers to a —C(O)-alkyl group, wherein alkyl is as defined above. Examples of alkylcarbonyl are methylcarbonyl, ethylcarbonyl, isopropylcarbonyl, tertbutylcarbonyl and the like.

The term "alkylcarbonyloxy" refers to a —O—C(O)-alkyl group, wherein alkyl is as defined above. Examples of alkylcarbonyloxy are methylcarbonyloxy, ethylcarbonyloxy, isopropylcarbonyloxy, tertbutylcarbonyloxy and the like.

The term "alkylsulfinyl" refers to a —SO-alkyl group, wherein alkyl is as defined above. Examples of alkylsulfinyl are methylsulfinyl, ethylsulfinyl, isopropylsulfinyl, tertbutylsulfinyl and the like.

The term "alkylsulfonyl" refers to a —$SO_2$-alkyl group, wherein alkyl is as defined above. Examples of alkylsulfonyl are methylsulfonyl, ethylsulfonyl, isopropylsulfonyl, tertbutylsulfonyl and the like.

The term "alkylthio" as employed herein alone or as a part of another group designates an alkyl group as defined above linked through a sulfur atom, i.e. —S-alkyl, wherein the alkyl group may be substituted by an aryl group as defined below. Examples of which include methylthio, ethylthio, isopropylthio, tertbutylthio, benzylthio, and the like.

The term "amino" refers to a —$NH_2$ group.

The term "aryl" means a mono-, bi- or tricyclic aromatic group, containing from six to fourteen carbon atoms in the ring portion, preferably from six to ten carbon atoms, wherein the monocyclic ring is aromatic, and at least one of the rings in the bi- or tricyclic ring is aromatic. Representative examples include phenyl, naphthyl, and indanyl, and the like.

The term "arylalkylene" refers to an alkylene group as defined above, substituted with an aryl group as defined above. Examples of arylalkylene are benzyl, phenethyl, phenylpropyl, and the like.

The term "carboxy" refers to a —COOH group.

The term "cyano" refers to a —CN group.

The term "cycloalkyl" is used in the present invention to designate a monocyclic or fused bicyclic, saturated or partially unsaturated (but not aromatic), monovalent hydrocarbon ring system of three to eight carbon ring atoms. Fused bicyclic hydrocarbon radical includes bridged ring systems. The term "cycloalkyl", as used in the present invention, also encompasses the above-mentioned ring systems wherein one or two ring carbon atoms are replaced by a —C(O)— or —C(S)— group. More specifically, the term cycloalkyl includes, but is not limited to, cyclopropyl, cyclobutyl, cyclopentyl, cyclohexyl, cyclohex-3-enyl, and the like.

The term "cycloalkylcarbonyl" refers to a —C(O)-cycloalkyl group, wherein cycloalkyl is as defined above. Examples of cycloalkylcarbonyl are cyclopropylcarbonyl, cyclobutylcarbonyl, cyclopentylcarbonyl, cyclohexylcarbonyl and the like.

The term "dialkylamino" refers to a —N(alkyl)$_2$ group, wherein alkyl is as defined above and wherein each alkyl may be the same or different. Examples of dialkylamino groups are dimethylamino, diethylamino, ethylmethylamino and the like.

The term "dialkylaminoalkyleneoxy" refers to a —O-alkylene-N(alkyl)$_2$ group, wherein alkyl and alkylene are as defined above and wherein each alkyl may be the same or different. Examples of dialkylaminoalkyleneoxy groups are dimethylaminomethoxy, diethylaminomethoxy, ethylmethylaminomethoxy, dimethylaminoethoxy, diethylaminoethoxy, ethylmethylaminoethoxy and the like.

The term "dialkylaminocarbonyl" refers to a —C(O)N(alkyl)$_2$ group, wherein alkyl is as defined above and wherein each alkyl may be the same or different. Examples of dialkylaminocarbonyl groups are dimethylaminocarbonyl, diethylaminocarbonyl, ethylmethylaminocarbonyl and the like.

The term "dialkylaminocarbonyloxy" refers to a —O—C(O)N(alkyl)$_2$ group, wherein alkyl is as defined above and wherein each alkyl may be the same or different. Examples of dialkylaminocarbonyloxy groups are dimethylaminocarbonyloxy, diethylaminocarbonyloxy, ethylmethylaminocarbonyloxy and the like.

The terms "halogen" and "halo" refer to any one of F, Cl, Br and I.

The term "heteroaryl" means a monocyclic, fused bicyclic, or fused tricyclic, group of 5 to 14 ring atoms, preferably from 5 to 6 ring atoms, containing one or more, specifically one, two, three, or four ring heteroatoms independently selected from O, N and S, and the remaining ring atoms being carbon. In the case of monocyclic heteroaryl groups the ring will be aromatic and in the case of fused bicyclic or fused tricyclic groups at least one of the fused rings will be aromatic. One or two ring atoms of any nonaromatic rings may be replaced by a —C(O)— or —C(S)—, group. Examples of heteroaryl groups are pyridine, furane, thiophene, quinoline, tetrahydroquinoline and the like The term "heterocyclyl" means a saturated or partially unsaturated (but not aromatic) monocyclic group of 3 to 8 ring atoms, preferably 5 to 7 ring atoms, or a saturated or partially unsaturated (but not aromatic) fused bicyclic group of 5 to 12 ring atoms in which one or more, specifically one, two, three of four ring heteroatoms are independently selected from N, O, and S. The heteroatoms may be substituted forming —S(O)n- (n is 0, 1, or 2). One or two ring atoms may be replaced by a —C(O)—, —C(S)—, or —C(=NH)— group. Fused bicyclic radical includes bridged ring systems. Examples of heterocyclyl are morpholinyl, piperidinyl, piperazinyl, and pyrrolidinyl.

The term "hydroxyalkyleneoxy" refers to a —O-alkylene-OH group, wherein alkylene is as defined above. Examples of hydroxyalkyleneoxy are hydroxymethoxy, 2-hydroxyethoxy, 3-hydroxypropoxy and the like.

The term "hydroxyl" or "hydroxyl" refers to a —OH group.

As used herein, the term "pharmaceutically acceptable salt" embraces salts with a pharmaceutically acceptable acid or base, which are synthesized from the parent compound which contains an acidic moiety by addition of a pharmaceutically acceptable base, or which are synthesized from the parent compound which contains a basic moiety by addition of a pharmaceutically acceptable acid. Pharmaceutically acceptable acids include both inorganic acids, for example, hydrochloric, sulfuric, phosphoric, diphosphoric, hydrobromic, hydroiodic, and nitric acid, and organic acids, for example, citric, fumaric, maleic, malic, mandelic, ascorbic, oxalic, succinic, tartaric, benzoic, acetic, methanesulfonic (mesylate), ethanesulfonic, benzenesulfonic (besylate), or p-toluenesulfonic (tosylate) acid. Pharmaceutically acceptable bases include alkali metal (e.g., sodium or potassium) and alkali earth metal (e.g., calcium or magnesium) hydroxides and organic bases, such as alkyl amines, arylalkyl amines, and heterocyclic amines. For instance, pharmaceutically acceptable salts of compounds provided herein are synthesized from the parent compound which contains a basic or an acid moiety by conventional chemical methods. Generally, such salts are, for example, prepared by reacting the free base or free acid forms of these compounds with a stoichiometric amount of the appropriate acid or base, respectively, in water or in an organic solvent or in a mixture of the two. Preferably, the pharmaceutically acceptable salt is the mesylate.

All stereoisomers of the compounds of this invention are contemplated either alone or as mixtures thereof. The process of preparation can utilize racemates, enantiomers, or diastereomers as starting materials. When diastereomeric or enantiomeric products are prepared, they can be separated by conventional methods, for example, chromatographic or functional crystallization.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon or $^{15}$N-enriched nitrogen are within the scope of this invention.

Compounds of Formula (I)

In a first aspect, the present invention is directed to a compound of formula (I):

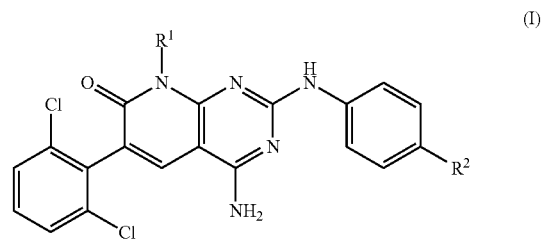

(I)

wherein
R$^1$ is selected from the group consisting of
  H;
  C$_1$-C$_6$ alkyl optionally substituted with one, two or three substituents independently selected from the group consisting of hydroxy; C$_1$-C$_6$ alkoxy, C$_1$-C$_6$ alkylthio, di(C$_1$-C$_6$ alkyl)amino, C$_1$-C$_6$ alkoxycarbonyl, cyano, and F;
  C$_3$-C$_8$ cycloalkyl optionally substituted with one, two or three substituents independently selected from the group consisting of hydroxy; C$_1$-C$_6$ alkoxy, C$_1$-C$_6$ alkylthio, C$_1$-C$_6$ alkoxycarbonyl, di(C$_1$-C$_6$ alkyl)amino, cyano, and F;
  C$_3$-C$_8$ cycloalkyl-C$_1$-C$_3$ alkylene, wherein the cycloalkyl is optionally substituted with one, two or three substituents independently selected from the group consisting of hydroxy; C$_1$-C$_6$ alkoxy, C$_1$-C$_6$ alkylthio, C$_1$-C$_6$ alkoxycarbonyl, di(C$_1$-C$_8$ alkyl)amino, cyano, and F;
  C$_6$-C$_{14}$ aryl optionally substituted with one, two or three substituents independently selected from the group consisting of C$_1$-C$_6$ alkyl, C$_1$-C$_6$ alkoxy, C$_1$-C$_6$ alkylthio, F, Cl, Br, C$_1$-C$_6$ alkoxycarbonyl, C$_1$-C$_6$ alkylcarbonyl, C$_3$-C$_8$ cycloalkylcarbonyl, C$_1$-C$_6$ alkylcarbonyloxy, amino, C$_1$-C$_6$ alkylamino, di(C$_1$-C$_6$ alkylamino, di(C$_1$-C$_6$ alkyl)aminocarbonyl, cyano, hydroxyl, hydroxy-C$_1$-C$_6$ alkyleneoxy, carboxy, C$_1$-C$_6$ alkylsulfonyl, C$_1$-C$_6$ alkylsulfinyl di(C$_1$-C$_6$ alkyl)aminocarbonyloxy, di(C$_1$-C$_6$ alkyl)amino-C$_1$-C$_6$ alkyleneoxy, C$_1$-C$_6$ alkoxycarbonyl, and C$_1$-C$_6$ alkoxy-C$_1$-C$_6$ alkyleneoxy;
  C$_6$-C$_{14}$ aryl-C$_1$-C$_3$ alkylene, wherein the aryl is optionally substituted with one, two or three substituents independently selected from the group consisting of C$_1$-C$_6$ alkyl, C$_1$-C$_6$ alkoxy, C$_1$-C$_6$ alkylthio, F, Cl, Br, C$_1$-C$_6$ alkoxycarbonyl, C$_1$-C$_6$ alkylcarbonyl, C$_3$-C$_8$ cycloalkylcarbonyl, C$_1$-C$_6$ alkylcarbonyloxy, amino, C$_1$-C$_6$ alkylamino, di(C$_1$-C$_6$ alkyl)amino, di(C$_1$-C$_6$ alkyl)aminocarbonyl, cyano, hydroxyl, hydroxy-C$_1$-C$_6$ alkyleneoxy, carboxy, C$_1$-C$_6$ alkylsulfonyl, C$_1$-C$_6$ alkylsulfinyl, di($C_1$-$C_6$ alkyl)aminocarbonyloxy, di($C_1$-$C_6$ alkyl)amino-$C_1$-$C_6$ alkyleneoxy, $C_1$-$C_6$ alkoxycarbonyl, and $C_1$-$C_6$ alkoxy-$C_1$-$C_6$ alkyleneoxy;

3- to 8-membered monocyclic or 5- to 12-membered bicyclic saturated or partially saturated heterocyclyl which contains from 1 to 4 heteroatoms in the ring independently selected from the group consisting of N, O, and S, and wherein the heterocyclyl is optionally substituted with one, two or three substituents independently selected from the group consisting of hydroxy; $C_1$-$C_6$ alkoxy, $C_1$-$C_6$ alkylthio, $C_1$-$C_6$ alkoxycarbonyl, di($C_1$-$C_6$ alkyl)amino, cyano, and F;

heterocyclyl-$C_1$-$C_3$ alkylene, wherein the heterocyclyl is a 3- to 8-membered monocyclic or 5- to 12-membered bicyclic saturated or partially saturated ring system which contains from 1 to 4 heteroatoms in the ring independently selected from the group consisting of N, O, and S as defined above, and wherein the heterocyclyl-$C_1$-$C_3$ alkyl is optionally substituted at the heterocyclyl moiety with one, two or three substituents independently selected from the group consisting of hydroxy; $C_1$-$C_6$ alkoxy, $C_1$-$C_6$ alkylthio, $C_1$-$C_6$ alkoxycarbonyl, di($C_1$-$C_6$ alkyl)amino, cyano, and F;

5- to 6-membered monocyclic or 8- to 14-membered bicyclic heteroaryl which contains from 1 to 4 heteroatoms in the ring system independently selected from the group consisting of N, O, and S, and wherein the heteroaryl is optionally substituted with one, two or three substituents independently selected from the group consisting of $C_1$-$C_6$ alkyl, $C_1$-$C_6$ alkoxy, $C_1$-$C_6$ alkylthio, F, Cl, Br, $C_1$-$C_6$ alkoxycarbonyl, $C_1$-$C_6$ alkylcarbonyl, $C_3$-$C_8$ cycloalkylcarbonyl, $C_1$-$C_6$ alkylcarbonyloxy, amino, $C_1$-$C_6$ alkylamino, di($C_1$-$C_6$ alkyl)amino, di($C_1$-$C_6$ alkyl)aminocarbonyl, cyano, hydroxyl, hydroxy-$C_1$-$C_6$ alkyleneoxy, carboxy, $C_1$-$C_6$ alkylcarbonyloxy, $C_1$-$C_6$ alkylsulfonyl, $C_1$-$C_6$ alkylsulfinyl, di($C_1$-$C_6$ alkyl)aminocarbonyloxy, di($C_1$-$C_6$ alkyl)amino-$C_1$-$C_6$ alkyleneoxy, $C_1$-$C_6$ alkoxycarbonyl, and $C_1$-$C_6$ alkoxy-$C_1$-$C_6$ alkyleneoxy; and heteroaryl-$C_1$-$C_3$ alkylene, wherein the heteroaryl is a 5- to 6-membered monocyclic or 8- to 14-membered bicyclic ring system which contains from 1 to 4 heteroatoms in the ring independently selected from the group consisting of N, O, and S, and wherein the heteroaryl is optionally substituted with one, two or three substituents independently selected from the group consisting of $C_1$-$C_6$ alkyl, $C_1$-$C_6$ alkoxy, $C_1$-$C_6$ alkylthio, F, Cl, Br, $C_1$-$C_6$ alkoxycarbonyl, $C_1$-$C_6$ alkylcarbonyl, $C_3$-$C_8$ cycloalkylcarbonyl, $C_1$-$C_6$ alkylcarbonyloxy, amino, $C_1$-$C_6$ alkylamino, di($C_1$-$C_6$ alkyl)amino, di($C_1$-$C_6$ alkyl)aminocarbonyl, cyano, hydroxyl, hydroxy-$C_1$-$C_6$ alkyleneoxy, carboxy, $C_1$-$C_6$ alkylcarbonyloxy, $C_1$-$C_6$ alkylsulfonyl, $C_1$-$C_6$ alkylsulfinyl, di($C_1$-$C_6$ alkyl)aminocarbonyloxy, di($C_1$-$C_6$ alkyl)amino-$C_1$-$C_6$ alkyleneoxy, $C_1$-$C_6$ alkoxycarbonyl, and $C_1$-$C_6$ alkoxy-$C_1$-$C_6$ alkyleneoxy;

$R^2$ is selected from the group consisting of

H; Cl, Br, I; —$NR^3R^4$; and —$OR^5$;

where $R^3$ is H and $R^4$ is selected from the group consisting of H and —$C_1$-$C_6$ alkylene-$NR^6R^7$;

or $R^3$ and $R^4$ together with the nitrogen atom to which they are attached form a saturated or partially saturated 3- to 8-membered monocyclic or 5- to 12-membered bicyclic heterocyclyl which contains from 1 to 4 heteroatoms in the ring system independently selected from the group consisting of N, O, and S, and which is optionally substituted with one, two or three substituents independently selected from the group consisting of $C_1$-$C_6$ alkoxy, $C_1$-$C_6$ alkylthio, $C_1$-$C_6$ alkoxycarbonyl, di($C_1$-$C_6$ alkyl)amino, cyano, and F;

$R^5$ is —$C_1$-$C_6$ alkylene-$NR^6R^7$;

$R^6$ is selected from the group consisting of H and $C_1$-$C_6$ alkyl;

$R^7$ is $C_1$-$C_6$ alkyl;

or $R^6$ and $R^7$ together with the nitrogen atom to which they are attached form a 3- to 8-membered saturated or partially saturated monocyclic heterocyclyl which contains form 1 to 4 heteroatoms in the ring system independently selected from the group consisting of N, O, and S, and which is optionally substituted with one, two or three substituents independently selected from the group consisting of $C_1$-$C_6$ alkoxy, $C_1$-$C_6$ alkylthio, $C_1$-$C_6$ alkoxycarbonyl, di($C_1$-$C_6$ alkyl)amino, cyano, and F;

or a stereoisomer or a pharmaceutically acceptable salt thereof.

In one embodiment, the present invention provides a compound of formula (I) wherein $R^1$ is selected from the group consisting of H; $C_1$-$C_6$ alkyl optionally substituted with one, two or three substituents independently selected from the group consisting of hydroxyl, $C_1$-$C_6$ alkoxy, $C_1$-$C_6$ alkylthio, di($C_1$-$C_6$ alkyl)amino, $C_1$-$C_6$ alkoxycarbonyl, cyano, and F; $C_6$-$C_{10}$ aryl-$C_1$-$C_3$ alkylene wherein the aryl moiety is optionally substituted with one, two or three substituents independently selected from the group consisting of $C_1$-$C_6$ alkyl, $C_1$-$C_6$ alkoxy, $C_1$-$C_6$ alkylthio, F, Cl, Br, $C_1$-$C_6$ alkoxycarbonyl, $C_1$-$C_6$ alkylcarbonyl, $C_3$-$C_8$ cycloalkylcarbonyl, $C_1$-$C_6$ alkylcarbonyloxy, amino, $C_1$-$C_6$ alkylamino, di($C_1$-$C_6$ alkyl)amino, di($C_1$-$C_6$ alkyl)aminocarbonyl, cyano, hydroxyl, hydroxy-$C_1$-$C_6$ alkyleneoxy, carboxy, $C_1$-$C_6$ alkylcarbonyloxy, $C_1$-$C_6$ alkylsulfonyl, $C_1$-$C_6$ alkylsulfinyl, di($C_1$-$C_6$ alkyl)aminocarbonyloxy, di($C_1$-$C_6$ alkyl)amino-$C_1$-$C_6$ alkyleneoxy, $C_1$-$C_6$ alkoxycarbonyl, and $C_1$-$C_6$ alkoxy-$C_1$-$C_6$ alkyleneoxy.

In another embodiment, the present invention provides a compound of formula (I) wherein $R^1$ is selected from the group consisting of H, unsubstituted $C_1$-$C_3$ alkyl, and unsubstituted $C_6$-$C_{10}$ aryl-$C_1$-$C_3$ alkylene.

In still another embodiment, the present invention provides a compound of formula (I) wherein $R^1$ is selected from the group consisting of H, methyl, and benzyl, preferably H and methyl, more preferably methyl.

In another embodiment, the present invention provides a compound of formula (I) wherein $R^2$ is selected from the group consisting of H; Br; —$NR^3R^4$; and —$OR^5$; wherein $R^3$ is H; $R^4$ is selected from the group consisting of H and —$C_1$-$C_6$ alkylene-$NR^6R^7$; or $R^3$ and $R^4$ together with the nitrogen atom to which they are attached form a saturated 5- to 7-membered monocyclic heterocyclyl which contains from 1 to 2 heteroatoms in the ring system independently selected from the group consisting of N, O, and S, and which is optionally substituted with one, two or three substituents independently selected from the group consisting of $C_1$-$C_6$ alkoxy, $C_1$-$C_6$ alkylthio, $C_1$-$C_6$ alkoxycarbonyl, di($C_1$-$C_6$ alkyl)amino, cyano, and F; $R^5$ is —$C_1$-$C_6$ alkylene-$NR^6R^7$; and wherein $R^6$ and $R^7$ together with the nitrogen atom to which they are attached form a 5- to 7-membered saturated monocyclic heterocyclyl which contains from 1 to 2 heteroatoms in the ring system selected from the group consisting of N and O, and which is optionally substituted with one, two or three substituents independently selected from the group consisting of $C_1$-$C_6$ alkoxy, $C_1$-$C_6$ alkylthio, $C_1$-$C_6$ alkoxycarbonyl, di($C_1$-$C_6$ alkyl)amino, cyano, and F.

In a particular embodiment, the present invention provides a compound of formula (I) wherein $R^2$ is selected from the group consisting of H; Br; $NR^3R^4$; and $-OR^5$; wherein $R^3$ is H; $R^4$ is selected from the group consisting of H and $-C_1-C_3$ alkylene-$NR^6R^7$, more preferably $-(CH_2)_2-NR^6R^7$; or $R^3$ and $R^4$ together with the nitrogen atom to which they are attached form a saturated 5- to 7-membered monocyclic heterocyclyl which contains from 1 to 2 heteroatoms in the ring system independently selected from the group consisting of N, O, and S, and which is optionally substituted with one, two or three substituents independently selected from the group consisting of $C_1-C_6$ alkoxy, $C_1-C_3$ alkylthio, $C_1-C_3$ alkoxycarbonyl, di($C_1-C_3$ alkyl)amino, cyano, and F; $R^5$ is $-C_1-C_3$ alkylene-$NR^6R^7$, preferably $-(CH_2)_2-NR^6R^7$; and $R^6$ and $R^7$ together with the nitrogen atom to which they are attached form a 5- to 7-membered saturated monocyclic heterocyclyl which contains from 1 to 2 heteroatoms in the ring system selected from the group consisting of N and O, and which is optionally substituted with one, two or three substituents independently selected from the group consisting of $C_1-C_3$ alkoxy, $C_1-C_3$ alkylthio, $C_1-C_3$ alkoxycarbonyl, di($C_1-C_3$ alkyl)amino, cyano, and F.

In another particular embodiment, the present invention provides a compound of formula (I) wherein $R^2$ is selected from the group consisting of H; Br; $NR^3R^4$; and $-OR^5$; wherein $R^3$ is H; $R^4$ is selected from the group consisting of H and $-C_1-C_3$ alkylene-$NR^6R^7$, preferably H or $-(CH_2)_2-NR^6R^7$; or $R^3$ and $R^4$ together with the nitrogen atom to which they are attached form a heterocyclyl selected from the group consisting of morpholinyl, piperidinyl optionally substituted with $C_1-C_3$ alkyl, preferably unsubstituted or substituted with methyl, piperazinyl optionally substituted with $C_1-C_3$ alkyl, preferably substituted with methyl (preferably substituted on a nitrogen atom), and pyrrolidinyl; $R^5$ is $-C_1-C_3$ alkylene-$NR^6R^7$, preferably $-(CH_2)_2-NR^6R^7$; and $R^6$ and $R^7$ together with the nitrogen atom to which they are attached form a heterocyclyl selected from the group consisting of morpholinyl, piperidinyl optionally substituted with $C_1-C_3$ alkyl, piperazinyl optionally substituted with $C_1-C_3$ alkyl, more preferably substituted with methyl on a nitrogen atom, and pyrrolidinyl.

In another particular embodiment, the present invention provides a compound of formula (I) wherein $R^2$ is selected from the group consisting of H and $-NR^3R^4$ wherein $R^3$ and $R^4$ together with the nitrogen atom to which they are attached form a piperazinyl optionally substituted with $C_1-C_3$ alkyl, preferably methyl, wherein the substituent is preferably at the nitrogen atom.

In another particular embodiment, the present invention provides a compound of formula (I) wherein, $R^2$ is selected from the group consisting of $-NR^3R^4$ and $-OR^5$, wherein $R^3$ is H; $R^4$ is $-C_1-C_3$ alkylene-$NR^6R^7$; or $R^3$ and $R^4$ together with the nitrogen atom to which they are attached form a heterocyclyl selected from the group consisting of morpholinyl, piperidinyl optionally substituted with $C_1-C_3$ alkyl, preferably unsubstituted or substituted with methyl, piperazinyl optionally substituted with $C_1-C_3$ alkyl, preferably substituted with methyl (preferably substituted on a nitrogen atom), and pyrrolidinyl; $R^5$ is $-C_1-C_3$ alkylene-$NR^6R^7$; and $R^6$ and $R^7$ together with the nitrogen atom to which they are attached form a heterocyclyl selected from the group consisting of morpholinyl, piperidinyl optionally substituted with $C_1-C_3$ alkyl, preferably unsubstituted, piperazinyl optionally substituted with $C_1-C_3$ alkyl, preferably substituted with methyl (preferably substituted on a nitrogen atom), and pyrrolidinyl.

In another embodiment, the present invention provides a compound of formula (I) wherein, $R^2$ is selected from the group consisting of $-NR^3R^4$ and $-OR^5$, wherein $R^3$ is H; $R^4$ is $-C_1-C_3$ alkylene-$NR^6R^7$, preferably $-(CH_2)_2-NR^6R^7$; or $R^3$ and $R^4$ together with the nitrogen atom to which they are attached form a piperazinyl optionally substituted with $C_1-C_3$ alkyl, preferably substituted with methyl (preferably substituted on a nitrogen atom); $R^5$ is $-C_1-C_3$ alkylene-$NR^6R^7$, preferably $-(CH_2)_2-NR^6R^7$; and $R^6$ and $R^7$ together with the nitrogen atom to which they are attached form a morpholinyl.

In another embodiment, the present invention provides a compound of formula (I) wherein $R^2$ is a piperazinyl substituted with $C_1-C_3$ alkyl, preferably methyl. In another embodiment $R^2$ is 4-methyl-piperazin-1-yl.

In another particular embodiment of the present invention provides a compound of formula (I) wherein $R^1$ is $C_1-C_3$ alkyl, preferably methyl; and $R^2$ is selected from the group consisting of $-NR^3R^4$ and $-OR^5$, wherein $R^3$ is H; $R^4$ is $-(CH_2)_2-NR^6R^7$; or $R^3$ and $R^4$ together with the nitrogen atom to which they are attached form a heterocyclyl selected from the group consisting of morpholinyl, piperidinyl optionally substituted with methyl, piperazinyl optionally substituted methyl (preferably substituted on a nitrogen atom), and pyrrolidinyl, preferably the heterocyclyl is piperazinyl substituted with methyl, preferably on a nitrogen atom; $R^5$ is $-(CH_2)_2-NR^6R^7$; and $R^6$ and $R^7$ together with the nitrogen atom to which they are attached form a heterocyclyl selected from the group consisting of morpholinyl, piperidinyl, piperazinyl and pyrrolidinyl, preferably morpholinyl.

In another embodiment, the present invention is directed to a compound of formula (I) selected from the group consisting of:
  4-amino-6-(2,6-dichlorophenyl)-2-(phenylamino)pyrido[2,3-d]pyrimidin-7(8H)-one;
  4-amino-6-(2,6-dichlorophenyl)-8-methyl-2-(phenylamino)pyrido[2,3-d]pyrimidin-7(8H)-one;
  4-amino-8-benzyl-6-(2,6-dichlorophenyl)-2-(phenylamino)pyrido[2,3-d]pyrimidin-7(8H)-one;
  4-amino-2-(4-bromophenylamino)-6-(2,6-dichlorophenyl)-8-methylpyrido[2,3-d]pyrimidin-7(8H)-one;
  4-amino-6-(2,6-dichlorophenyl)-8-methyl-2-(4-(4-methylpiperazin-1-yl)phenylamino)pyrido[2,3-d]pyrimidin-7(8H)-one;
  4-amino-6-(2,6-dichlorophenyl)-8-methyl-2-(4-(2-morpholinoethylamino)-phenylamino)pyrido[2,3-d]pyrimidin-7(8H)-one;
  4-amino-6-(2,6-dichlorophenyl)-8-methyl-2-(4-(2-morpholinoethoxy)-phenylamino)pyrido[2,3-d]pyrimidin-7(8H)-one; and
  4-amino-2-(4-aminophenylamino)-6-(2,6-dichlorophenyl)-8-methylpyrido[2,3-d]pyrimidin-7(8H)-one;
or a stereoisomer or pharmaceutically acceptable salt thereof.

In another embodiment, the compound of formula (I) is selected from the group consisting of 4-amino-6-(2,6-dichloro phenyl)-8-methyl-2-(4-(2-morpholinoethoxy)-phenylamino)-pyrido[2,3-d]pyrimidin-7(8H)-one, 4-amino-6-(2,6-dichlorophenyl)-8-methyl-2-(4-(2-morpholinoethylamino)-phenylamino)pyrido[2,3-d]pyrimidin-7(8H)-one, and 4-amino-6-(2,6-dichlorophenyl)-

8-methyl-2-(4-(4-methylpiperazin-1-yl)phenylamino) pyrido[2,3-d]pyrimidin-7(8H)-one, preferably 4-amino-6-(2,6-dichlorophenyl)-8-methyl-2-(4-(4-methyl piperazin-1-yl)phenylamino)pyrido[2,3-d]pyrimidin-7(8H)-one, or a stereoisomer or pharmaceutically acceptable salt thereof.

Even more preferably, the compound of formula (I) is selected from the group consisting of 4-amino-6-(2,6-dichlorophenyl)-8-methyl-2-(4-(4-methylpiperazin-1-yl)phenylamino)pyrido[2,3-d]pyrimidin-7(8H)-one and 4-amino-6-(2,6-dichlorophenyl)-8-methyl-2-(4-(4-methylpiperazin-1-yl)phenylamino)pyrido[2,3-d]pyrimidin-7(8H)-one dimesylate.

Synthesis of Compounds of Formula (I)

Usually pyrido[2,3-d]pyrimidin-7(8H)-one derivatives are obtained through a multistep strategy in which the pyridine ring is constructed by condensation of a nitrile (IV) (bearing the desired substituent $R^8$) onto a preformed pyrimidine aldehyde (V) bearing substituent $R^9$ and a methylthio group which can later be substituted by $NH_2R^{10}$ substituent using an amine (VI) (retrosynthetic Scheme 1). Thus, for instance, compounds (III) are prepared using uracil as starting material in at least six steps.

2-methoxy-6-oxo-1,4,5,6-tetrahydropyridin-3-carbonitriles (IX) are obtained by reaction of an α,β-unsaturated ester (VII) and malonitrile (VIII, G=CN) in NaOMe/MeOH. Treatment of pyridones (IX) with guanidine systems (XI, $R^{14}$=H, alkyl, aryl, heteroaryl) affords 4-amino-pyrido[2,3-d]pyrimidines (XII, $R^{13}$=NH$_2$). On the other hand, we described an acyclic variation of the above protocol for the synthesis of pyridopyrimidines (XII, $R^{13}$=NH$_2$) based on the isolation of the corresponding Michael adduct (X, G=CN) and later cyclization with a guanidine (XI). This approach also allowed us to obtain 4-oxopyrido[2,3-d]pyrimidines by treatment of intermediates (X, G=COOMe), synthesized by Michael addition of α,β-unsaturated esters (VII) and methyl cyanoacetate (VIII, G=COOMe), with guanidine (XI). It has also been described a multicomponent microwave-assisted cyclocondensation affording systems (XII) and (XIII) via acyclic intermediates (X) (Scheme 2) [see for instance: Perez-Pi, I.; Berzosa, X.; Galve, I.; Teixidó, J.; Borrell, J. I. *Heterocycles* 2010, 82, 581-591 and the references therein].

Scheme 2

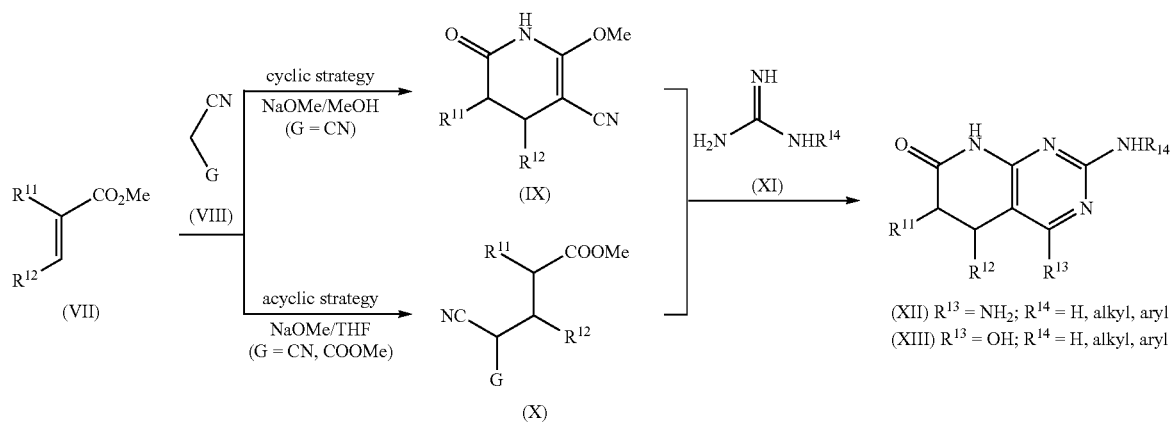

Scheme 1

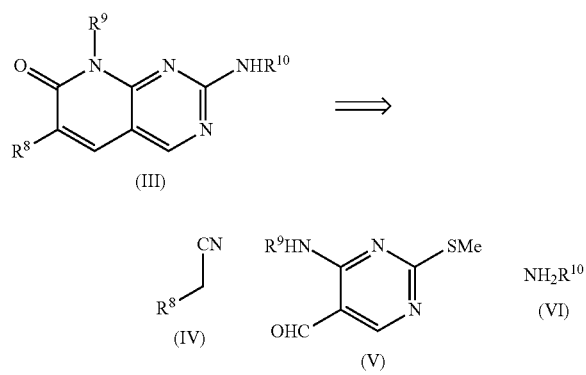

In this context, the research group to which the inventors belong has a broad experience in the synthesis of 5,6-dihydropyrido[2,3-d]pyrimidin-7-(8H)-ones (XII; $R^{13}$=NH$_2$) and (XIII; $R^{13}$=OH) from α,β-unsaturated esters (VII). Thus, in the so called cyclic strategy More recently, we have developed protocols for the dehydrogenation of 5,6-dihydropyrido[2,3-d]pyrimidin-7(8H)-ones to pyrido[2,3-d]pyrimidin-7(8H)-ones [*Heterocycles* 2010, 82, 581-591] and a methodology for the synthesis of 2-arylamino substituted 4-amino-5,6-dihydropyrido[2,3-d]pyrimidin-7(8H)-ones (XV) from α,β-unsaturated esters (VII), malononitrile (VIII), and an arylsubstituted guanidine (XI) via the corresponding 3-aryl substituted pyridopyrimidines (XIV), formed upon treatment of pyridones (IX) with the arylsubstituted guanidine (XI) in dioxane, which underwent the Dimroth rearrangement to the desired 4-aminopyridopyrimidines (XV) with NaOMe/MeOH. The overall yields of such three-step protocol are in general higher than the multicomponent reaction between an α,β-unsaturated ester (VII), malononitrile (VIII), and an arylsubstituted guanidine (XI) (Scheme 3) [Galve, I., Puig de la Bellacasa, R., Sanchez-Garcia, D., Batllori, X., Teixidó, J., Borrell, J. I. *Mol. Diver.* 2012, 16, 639-649].

Scheme 3

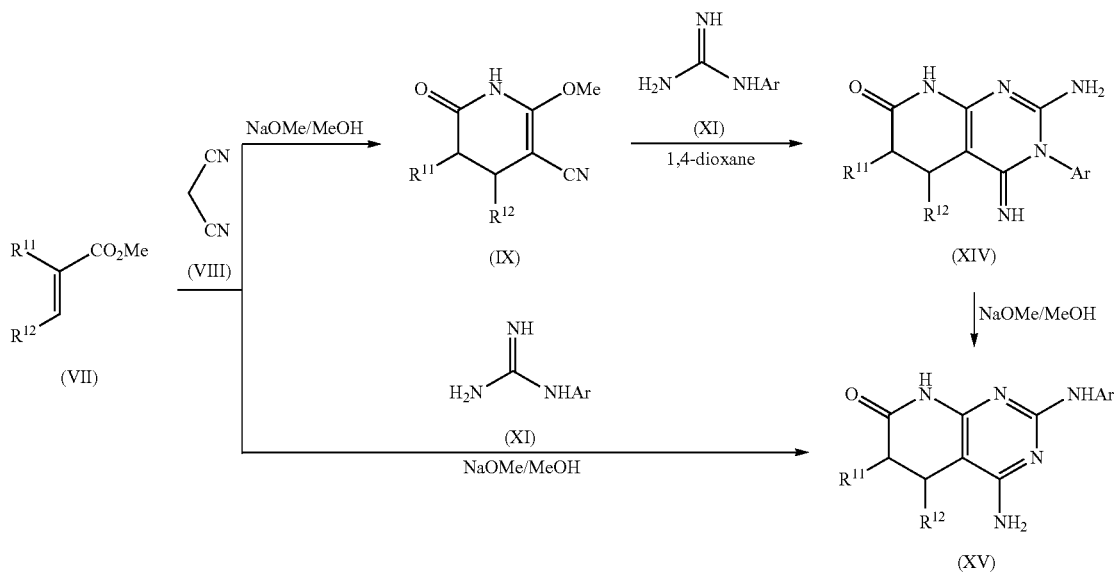

2-Arylamino-4-amino-5,6-dihydropyrido[2,3-d]pyrimidin-7(8H)-ones (XV), or their analogues (XVI) are an interesting class of heterocyclic compounds that cannot be made through the general strategy depicted in Scheme 1 because the starting pyrimidine aldehyde (V) should bear two amino groups at positions C2 and C4 (see structure (XVII) below) thus rendering impossible the regiospecific cyclization needed to afford compounds (XVI). Consequently, until now, the only methodology capable to synthesize 4-aminopyrido[2,3-d]pyrimidines is the one reported by our group.

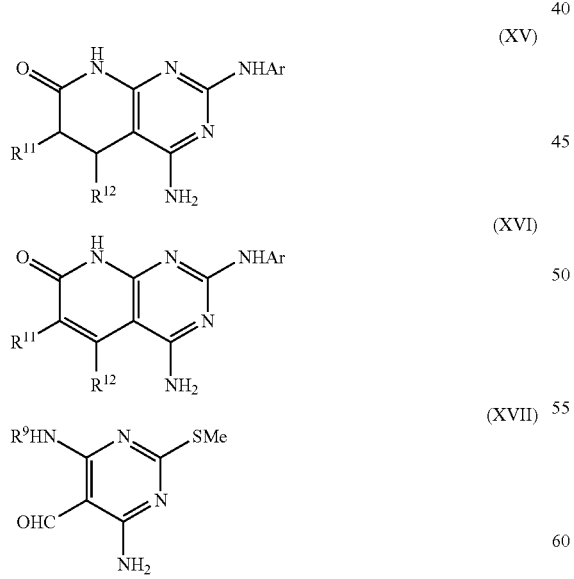

Thus, in a second aspect, the present invention relates to a process for the preparation of a compound of formula (I) as defined above, or a stereoisomer or pharmaceutically acceptable salt thereof, which comprises:

a) reacting a compound of formula (II)

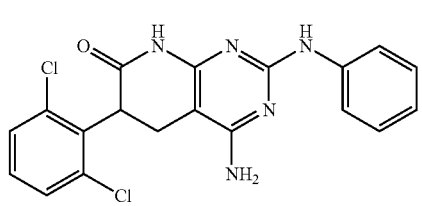

with a dehydrogenating agent to give a compound of formula (Ia)

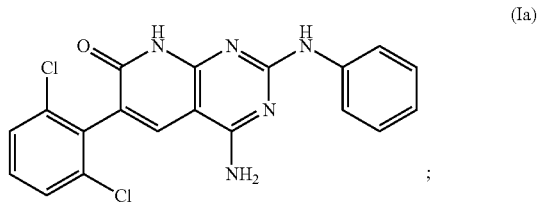 [SMILES: Nc1nc(Nc2ccccc2)nc2[nH]c(=O)c(-c3c(Cl)cccc3Cl)cc12 ; ";"]

b) when in the compound of formula (I) $R^1$ is different from H, reacting the compound of formula (Ia) in the presence of a base with a compound $R^1$-LG, wherein LG is selected from the group consisting of Cl, Br, I, O-tosyl and O-triflate, to give a compound of formula (Ib)

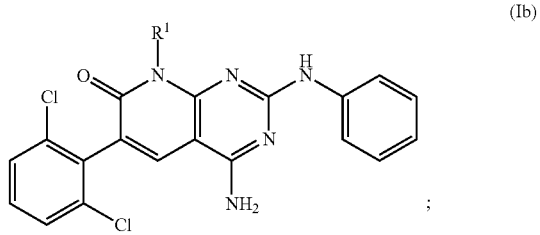

c) when in the compound of formula (I) $R^2$ is different from H, reacting the compound of formula (Ib) with a halogenating agent to give a compound of formula (Ic)

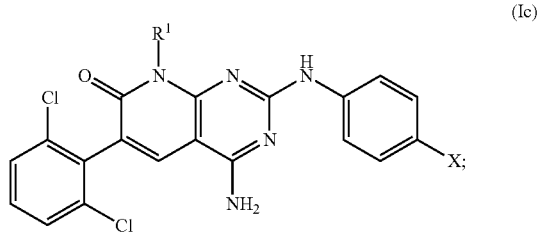

(Ic)

wherein X is selected from the group consisting of Cl, Br and I; and d) when in the compound of formula (I) $R^2$ is neither H nor X (being X an atom selected from the group consisting of Cl, Br and I), reacting the compound of formula (Ic) in the presence of a copper catalyst with a compound $R^3R^4$—NH to give a compound of formula (Id)

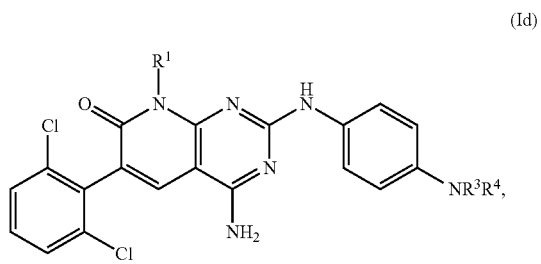

(Id)

or reacting the compound of formula (Ic) with a compound $R^5$—OH to give a compound of formula (Ie)

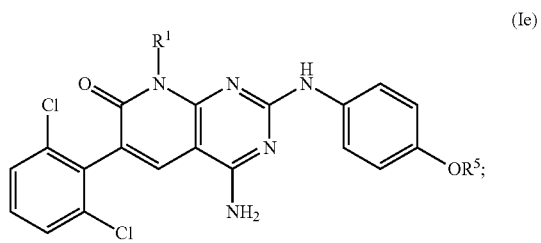

(Ie)

wherein
$R^1$-$R^5$ are as defined above for the compounds of formula (I).

Compounds (Ia)-(Ie) depicted above are particular definitions of the general formula (I).

The starting material used for the synthesis compounds of formula (I) according to the present invention, is the compound of formula (II), i.e. 4-amino-6-(2,6-dichlorophenyl)-2-(phenylamino)-5,6-dihydropyrido[2,3-d]pyrimidin-7(8H)-one, whose synthesis has been previously described [Galve, I., Puig de la Bellacasa, R., Sanchez-Garcia, D., Batllori, X., Teixidó, J., Borrell, J. I. Mol. Diver. 2012, 16, 639-649].

Step a) is an aromatization reaction that comprises reacting the compound of formula (II) with a dehydrogenating agent. This reaction may be carried using standard techniques known to the person skilled in the art.

The dehydrogenating agent is an organic or inorganic compound capable of removing the hydrogen atoms at the carbon atom on position 5 and 6 in the compound of formula (II) to give the corresponding compound of formula (Ia) depicted above. Such agents are well known to the expert in the field.

In one embodiment, the dehydrogenating agent is selected from the group consisting of activated $MnO_2$, NaH in dimethylsulfoxide (DMSO), $Na_2SO_3$ in dimethylsulfoxide (DMSO), 2,3-dichloro-5,6-dicyano-1,4-benzoquinone (DDQ) in dichloromethane, and Pd on carbon in acetic acid, preferably, the dehydrogenating agent is selected from NaH in dimethylsulfoxide and $Na_2SO_3$ in dimethylsulfoxide. Particular reaction conditions for step a) have been described, e.g. for activated $MnO_2$ [P. Victory, A. Crespo, R. Nomen, and J. I. Borrell, Afinidad, 1989, 46, 107], NaH in DMSO or $Na_2SeO_3$ in DMSO [Perez-Pi, I.; Berzosa, X.; Galve, I.; Teixido, J.; Borrell, J. I. Heterocycles 2010, 82, 581-591]. Preferred reaction conditions are NaH (60% dispersion in mineral oil) in DMSO as solvent, preferably between 80° C. and 120° C., more preferably at 100° C., preferably between 3 h to 6 h, more preferably for 4 hours, and preferably protected from moisture.

Activated $MnO_2$ can be obtained from commercial suppliers or can be prepared as described by J. Attenburrow [J. Chem. Soc. Perkin Trans. I, 1952, 1104]. Activated $MnO_2$ is considered to be an amorphous hydrate, containing about 4-7% of excess moisture (U.S. Pat. No. 3,702,889).

Step b) is performed when in the compound of formula (I) $R^1$ is different from H. This step comprises reacting the compound of formula (Ia) in the presence of a base with a compound $R^1$-LG, wherein $R^1$ is as defined above and LG is selected from the group consisting of Cl, Br, I, O-tosyl and O-triflate, to give a compound of formula (Ib). This step can be performed by a variety of methods such as treatment with a base (e.g., NaH, $Na_2CO_3$, $CsCO_3$, and the like) in an appropriate solvent (e.g., DMSO, DMF, and the like) followed by addition of $R^1$-LG. Preferably, step b) is performed using DMSO as the solvent and NaH as the base. Particularly preferred compounds $R^1$—X are those wherein LG is selected from the group consisting of I, Br, Cl, tosylate, mesylate or triflate, such as methyl iodide. In a particular embodiment, step b) is carried out at room temperature.

In the case of $R^1$ being optionally substituted aryl or optionally substituted heteroaryl radicals, step b) should be carried out by reaction of the compound of formula (Ia) with an aryl or heteroaryl iodide, in the presence of $Cu_2I_2$ and 8-hydroxyquinoline as catalyst in DMSO as solvent [Filipski, K. J.; Kohrt, J. T.; Casimiro-Garcia, A.; Van Huis, C. A.; Dudley, D. A.; Cody, W. L.; Bigge, C. F.; Desiraju, S.; Sun, S.; Maiti, S. N.; Jaber, M. R.; Edmunds, J. J., Tet. Lett. 2006, 47, 7677-7680].

Step c) is performed when in the compound of formula (I) $R^2$ is different from H. This step is a regioespecific halogenation in the para position of the 2-phenylamino substituent in the compound of formula (Ib). This step comprises reacting the compound of formula (Ib) with a halogenating agent to give a compound of formula (Ic). Halogenating agents are known in the art and typically consist in the use of the corresponding N-halo succinimide or the corresponding $X_2$, wherein X and "halo" is selected from the group of I, Br, Cl, preferably Br. Preferably, the halogenating agent is a brominating agent, i.e. X is Br. Preferably, the brominating agent is selected from the group consisting of $Br_2$ in acetic acid or N-bromosuccinimide in acetic acid, more preferably, Br₂ in acetic acid. Preferred reaction conditions are the use of between 0.8:1.5 and 1.5:0.8 molar amounts of the corresponding pyrido[2,3-d]pyrimidine (Ib) with respect to bromine in acetic acid, preferably 2M bromine in acetic acid solution, preferably between 0.9:1.1 and 1.1:0.9 molar amounts of the corresponding pyrido[2,3-d]pyrimidine (Ib) with respect to bromine in acetic acid, preferably 2M bromine in acetic acid solution, even more preferably equimolar amounts of the corresponding pyrido[2,3-d]pyrimidine (Ib) with respect to bromine in acetic acid, preferably 2M bromine in acetic acid solution. This reaction may be carried out in the presence of an organic solvent such as 1,4-dioxane or, THF In a particular embodiment, step c) is carried out at room temperature.

Finally, step d) is performed when in the compound of formula (I) $R^2$ is neither H nor X, wherein X is selected from Cl, Br and I, preferably X is Br. This step comprises the substitution of the bromine atom in the compounds of formula (Ic) by using Ullman reaction conditions. Thus, step d) is carried out by reacting the compound of formula (Ic) in the presence of a copper catalyst with a compound $R^3R^4$—NH, wherein $R^3$ and $R^4$ are as defined above for the compounds of formula (I), to give a compound of formula (Id), or reacting the compound of formula (Ic) with a compound $R^5$—OH, wherein $R^5$ is as defined above for the compounds of formula (I), to give a compound of formula (Ie). Preferably, the copper catalyst of is metallic copper, copper-bronze, $Cu_2Br_2$, $Cu_2O$, $Cu_2I_2$, preferably $Cu_2I_2$, and the reaction is performed in the presence of a base, such as $K_2CO_3$, $Na_2CO_3$, $CsCO_3$, and the like, preferably $K_2CO_3$, and a ligand selected from the group consisting of L-proline, ethyleneglycol, N,N-dimethylcyclohexane-1,2-diamine, and N,N-diethylsalicylamide, or the like, preferably, L-proline [J. Kim and S. Chang, *Chem. Commun.* 2008, 3052-3054]. Step d) may be carried out in an organic solvent such as dimethylsulfoxide, dimethylformamide, preferably dimethylsulfoxide. The reaction is preferably performed with heating, such as between 60° C. and 200° C., preferably between 60° C. and 100° C. In a particular embodiment, the heating is achieved by means of microwave irradiation, but conventional heating means may also be employed.

The compounds of formula (I) may be synthesized using standard synthetic methods known in the art in combination with the methods described herein. In addition, solvents, temperatures and other reaction conditions presented herein may be varied by those skilled in the art.

Intermediate compounds (Ib) and (Ic) as defined above, preferably compound (Ib) and compound (Ic) wherein X is Br, are also new compounds object of the present invention.

Pharmaceutical Compositions/Formulations and Administration

In another aspect, the present invention provides a pharmaceutical composition comprising a compound of formula (I) as defined above, or a stereoisomer or pharmaceutically acceptable salt thereof, and one or more pharmaceutically acceptable excipients.

The term "pharmaceutically acceptable excipient" refers to a vehicle, diluent, or adjuvant that is administered with the active ingredient. Such pharmaceutical excipients can be sterile liquids, such as water and oils, including those of petroleum, animal, vegetable, or synthetic origin, such as peanut oil, soybean oil, mineral oil, sesame oil, and similars. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 21st Edition, 2005.

Compounds of the invention may be administered by the oral, sublingual, parenteral, subcutaneous, intramuscular, intravenous, transdermal, intranasal, intraocular, and/or rectal routes. The compounds may be administered alone or in combination with one or more other compounds of the invention or one or more other drugs.

Doses of the compounds of the invention may be expressed either in mg of compound per kg of body weight or in mg of compound per square meter of body surface. The article from Reagan-Shaw S. "Dose translation from animal to human studies revisited". FASEB J 2007, 22:659-661 provides the standard conversion factors used to convert mg/kg to mg/m².

Dose (mg/kg)×$Km$=Dose (mg/m²)

The article also explains that this conversion is the basis for converting dose in a first animal species to dose in a second animal species (allometric dose translation). Thus, animal dose (AD) in mg/kg can be converted to human equivalent dose (HED) in mg/kg using the following formula:

$$HED\ (mg/kg) = AD\ (mg/kg) \times \frac{Animal\ K_m}{Human\ K_m}$$

wherein the $K_m$ for each species is shown in Table 1 (data extracted from Reagan-Shaw S. Dose translation from animal to human studies revisited. FASEB 0.12007, 22:659-661).

TABLE 1

| $K_m$ factor for conversion of AD to HED | | |
|---|---|---|
| Species | | $K_m$ factor |
| Human | Adult | 37 |
|  | Child | 25 |
| Baboon |  | 20 |
| Dog |  | 20 |
| Monkey |  | 12 |
| Rabbit |  | 12 |
| Guinea pig |  | 8 |
| Rat |  | 6 |
| Hamster |  | 5 |
| Mouse |  | 3 |

Suitable doses of the compounds of the present invention may be determined by the skilled person and, in an embodiment of the present invention, may be administered at a dose of from 1 to 50 mg/kg/day, preferably from 2 to 10 mg/kg/day, more preferably from 2 to 5 mg/kg/day in mice, which corresponds to general doses in mammals of 3 to 150 mg/m²/day, preferably from 6 to 30 mg/m²/day, more preferably from 6 to 15 mg/m²/day. In adult humans, these doses correspond to 0.081 to 4.05 mg/kg/day, preferably from 0.162 to 0.811 mg/kg/day, more preferably from 0.162 to 0.405 mg/kg/day Pharmacological Activity LYN, SYK, and BTK kinases are considered as potential drug targets for the treatment of NHLs, in particular of CLL, MCL, FL and DLBCL. The compounds of formula (I) according to the present invention, which are inhibitors of LYN, SYK and BTK kinases, may be used for treating or preventing a condition in a mammal, including a human, of a NHL, in particular mature B cell neoplasms, more particularly CLL, MCL, FL and DLBCL.

Therefore, in another aspect, the present invention provides a compound of formula (I) as defined above, or a stereoisomer or pharmaceutically acceptable salt thereof, for use as a medicament.

The present invention also provides the use of a compound of formula (I) as defined above, or a stereoisomer or pharmaceutically acceptable salt thereof, in the manufacture of a medicament.

In another aspect, the present invention provides a compound of formula (I) as defined above, or a stereoisomer or pharmaceutically acceptable salt thereof, for use in the treatment and/or prevention of NHLs, preferably mature B cell neoplasms, more preferably a mature B cell neoplasm selected from the group consisting of CLL, MCL, FL and DLBCL.

The present invention also relates to the use of a compound of formula (I) as defined above, or a stereoisomer or pharmaceutically acceptable salt thereof, for manufacturing a medicament for the treatment and/or prevention of a non-Hodgkin's lymphoma, preferably mature B cell neoplasms, more preferably mature B cell neoplasms selected from the group consisting of CLL, MCL, FL and DLBCL.

The invention also relates to a method of treating, ameliorating or reducing the risk of Non-Hodgkin's lymphoma, preferably mature B cell neoplasms, more preferably mature B cell neoplasms selected from the group consisting of CLL, MCL, FL and DLBCL, in a subject in need thereof, the method comprising administering a therapeutically effective amount of a compound of formula (I) as defined above, or a stereoisomer or pharmaceutically acceptable salt thereof to said subject.

The following examples represent specific embodiments of the present invention. They do not intend to limit in any way the scope of the invention defined in the present description.

The following abbreviations are employed herein:
AcOH: acetic acid
DMSO: dimethylsulfoxide
EtOH: ethanol
EtOEt: diethyl ether
MeOH: methanol
cpm: counts per minute
$GI_{50}$: concentration of drug required to reduce cell growth by 50%

EXAMPLES

Materials and Methods $^1$H and $^{13}$C NMR spectra were recorded on a Varian 400-MR spectrometer that was operating at a field strength of 400 and 100.6 MHz, respectively. Chemical shifts were reported in parts per million (d) and coupling constants (0.1) were in Hz by using, in the case of $^1$H NMR spectroscopy, TMS as an internal standard, and in the case of $^{13}$C NMR spectroscopy the solvent at 39.5 ppm ($d_6$-DMSO) as an internal reference. Standard and peak multiplicities are designed as follows: s, singlet; d, doublet; t, triplet; q, quartet; br s, broad signal.

Automatic flash chromatography was performed in an Isco Combiflash medium pressure liquid chromatograph with RediSep' silica gel columns (35-70 μm) using a suitable mixture of solvents as eluent.

Microwave irradiation experiments were carried out in a Initiator™ (Biotage) microwave apparatus, operating at a frequency of 2.45 GHz with continuous irradiation power from 0 to 400 W. Reactions were carried out in 0.5, 2.5, 5, 20 mL glass tubes, sealed with aluminium/Teflon crimp tops, which can be exposed up to 250° C. and 20 bar internal pressure. Temperature was measured with an IR sensor on the outer surface of the process vial. After the irradiation period, the reaction vessel was cooled rapidly to 50° C. by air jet cooling.

Example 1

4-amino-6-(2,6-dichlorophenyl)-2-(phenylamino)pyrido[2,3-d]pyrimidin-7(8H)-one

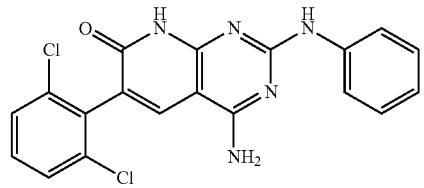 [SMILES: Nc1nc(Nc2ccccc2)nc2[nH]c(=O)c(-c3c(Cl)cccc3Cl)cc12]

A mixture of 200.1 mg (0.5 mmol) of 4-amino-6-(2,6-dichlorophenyl)-5,6-dihydro-2-(phenylamino)pyrido[2,3-d]pyrimidin-7(8H)-one (synthesized as described in Galve et al., Mol. Diver. 2012, 16, 639-649) and 60.0 mg (1.5 mmol) of sodium hydride (NaH) (60% dispersion in mineral oil) in 5 mL of anhydrous DMSO was heated for 4 hours at 100° C. protected from moisture. The resulting solution was cooled down, water (300 mL) was added and it was neutralized with AcOH. The resulting precipitate was filtered, washed with EtOH and EtOEt and dried in vacuo over phosphorus pentoxide to afford 173.3 mg (0.44 mmol, 87%) of 4-amino-6-(2,6-dichlorophenyl)-2-(phenylamino)pyrido[2,3-d]pyrimidin-7(8H)-one as a brownish solid.

$^1$H NMR (400 MHz, $d_6$-DMSO) δ 11.85 (br s, 1H), 9.26 (br s, 1H), 8.04 (s, 1H), 7.88 (d, J=7.7 Hz, 2H), 7.60-7.52 (m, 2H), 7.42 (dd, J=8.7, 7.5 Hz, 1H), 7.29 (br s, 2H), 7.27-7.18 (m, 2H), 6.92 (t, J=7.3 Hz, 1H). $^{13}$C NMR (100.6 MHz, $d_6$-DMSO) δ 161.3, 161.1, 159.5, 156.1, 140.6, 135.5, 135.4, 135.0, 130.3, 128.3, 128.0, 121.6, 121.4, 119.5, 91.3.

Example 2

4-amino-6-(2,6-dichlorophenyl)-8-methyl-2-(phenylamino)pyrido[2,3-d]pyrimidin-7(8H)-one

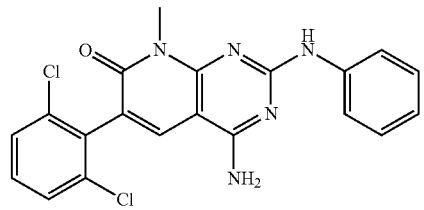 [SMILES: Cn1c(=O)c(-c2c(Cl)cccc2Cl)cc2c(N)nc(Nc3ccccc3)nc21]

To a solution of 280.2 mg (0.7 mmol) of 4-amino-6-(2,6-dichlorophenyl)-2-(phenylamino)pyrido[2,3-d]pyrimidin-7(8H)-one in 10 mL of anhydrous DMSO, 28.0 mg (0.7 mmol) of sodium hydride (NaH) (60% dispersion in mineral oil) were added and the mixture was stirred for 1 hour at room temperature under nitrogen atmosphere. After this period, 43.8 μL (0.7 mmol) of methyl iodide were added dropwise and then stirred overnight at room temperature. The reaction was quenched by addition of 300 mL of water and the resulting precipitate was filtered, washed with water and dried in vacuo over phosphorus pentoxide to afford 275.7 mg (0.67 mmol, 96%) of 4-amino-6-(2,6-dichlorophenyl)-8-methyl-2-(phenylamino)pyrido[2,3-d]pyrimidin-7(8H)-one as a brownish solid.

$^1$H NMR (400 MHz, d$_6$-DMSO) δ 9.41 (br s, 1H), 8.09 (s, 1H), 7.82 (d, J=8.5 Hz, 2H), 7.56 (d, J=7.9 Hz, 2H), 7.42 (t, J=7.6 Hz, 1H), 7.38 (br s, 2H), 7.28 (t, J=7.7 Hz, 2H), 6.95 (t, J=7.3 Hz, 1H), 3.59 (s, 3H). $^{13}$C NMR (100 MHz, d$_6$-DMSO) δ 161.7, 160.5, 159.07, 156.1, 140.4, 135.4, 135.3, 134.0, 130.3, 128.4, 128.0, 121.7, 120.1, 119.6, 91.6, 28.4.

Example 3

4-amino-8-benzyl-6-(2,6-dichlorophenyl)-2-(phenylamino)pyrido[2,3-d]pyrimidin-7(8H)-one

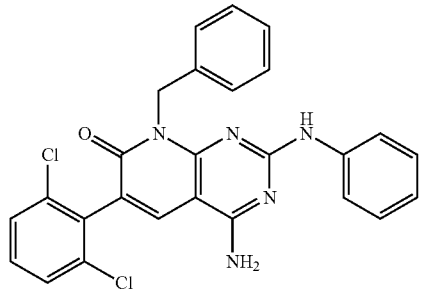 [SMILES: Nc1nc(Nc2ccccc2)nc2c1cc(-c1c(Cl)cccc1Cl)c(=O)n2Cc1ccccc1]

To a solution of 199.1 mg (0.5 mmol) of 4-amino-6-(2,6-dichlorophenyl)-2-(phenylamino)pyrido[2,3-d]pyrimidin-7(8H)-one in 7 mL of anhydrous DMSO, 20.0 mg (0.5 mmol) of sodium hydride (NaH) (60% dispersion in mineral oil) were added and the mixture was stirred for 1 hour at room temperature under nitrogen atmosphere. After this period, 60.6 μL (0.5 mmol) of benzyl bromide were added dropwise and then stirred overnight at room temperature. The reaction was quenched by addition of 300 mL of water and the resulting precipitate was filtered, washed with water and dried in vacuo over phosphorus pentoxide to afford 237.9 mg (0.49 mmol, 97%) of 4-amino-8-benzyl-6-(2,6-dichlorophenyl)-2-(phenylamino)pyrido[2,3-d]pyrimidin-7(8H)-one as a yellowish solid.

$^1$H NMR (400 MHz, d$_6$-DMSO) δ 9.37 (br s, 1H), 8.18 (s, 1H), 7.63 (d, J=7.2 Hz, 2H), 7.58 (d, J=8.0 Hz, 2H), 7.45 (dd, J=8.7, 7.5 Hz, 1H), 7.3 (br s, 2H), 7.32-7.17 (m, 7H), 6.95 (t, J=7.3 Hz, 1H), 5.53 (s, 2H). $^{13}$C NMR (100 MHz, d$_6$-DMSO) δ 161.7, 160.5, 159.1, 155.8, 140.1, 137.6, 135.4, 135.2, 134.5, 130.4, 128.3, 128.2, 128.1, 126.8, 121.8, 120.4, 119.7, 91.7, 43.8.

Example 4

4-amino-2-(4-bromophenylamino)-6-(2,6-dichlorophenyl)-8-methylpyrido[2,3-d]pyrimidin-7(8H)-one

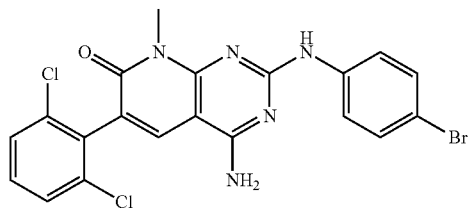 [SMILES: Cn1c(=O)c(-c2c(Cl)cccc2Cl)cc2c(N)nc(Nc3ccc(Br)cc3)nc21]

A dispersion of 412.3 mg (1.0 mmol) of 4-amino-6-(2,6-dichlorophenyl)-8-methyl-2-(phenylamino)pyrido[2,3-d]pyrimidin-7(8H)-one in 40 mL of acetic acid is treated with 0.50 mL (1.0 mmol) of bromine 2M in acetic acid solution for 2 hours at room temperature. The resulting solution is diluted with 1,4-dioxane (40 mL) and the solvent is removed by vacuum azeotropic distillation. A second 1,4-dioxane addition (40 mL) and vacuum distillation yields a white solid that is dispersed in water with ultrasound and mechanical stirring. And the resulting precipitate was filtered, washed with water and dried in vacuo over phosphorus pentoxide to afford 490.2 mg (0.5 mmol, quantitative) of 4-amino-2-(4-bromophenylamino)-6-(2,6-dichlorophenyl)-8-methylpyrido[2,3-d]pyrimidin-7(8H)-one as a white solid.

$^1$H NMR (400 MHz, d$_6$-DMSO) δ 9.60 (br s, 1H), 8.12 (s, 1H), 7.82 (d, J=9.0 Hz, 2H), 7.58 (d, J=8.0 Hz, 2H) 7.57 (br s, 2H), 7.50-7.42 (m, 3H), 3.60 (s, 3H). $^{13}$C NMR (100.6 MHz, d$_6$-DMSO) δ 161.1, 160.4, 158.1, 155.9, 139.5, 135.3, 135.1, 133.9, 131.2, 130.4, 128.1, 121.6, 120.6, 113.4, 91.7, 28.5.

Example 5

4-amino-6-(2,6-dichlorophenyl)-8-methyl-2-(4-(4-methylpiperazin-1-yl)phenylamino)pyrido[2,3-d]pyrimidin-7(8H)-one

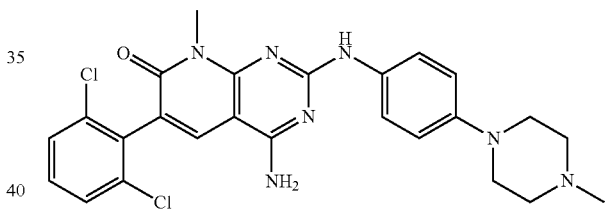

A mixture of 196.4 mg (0.4 mmol) of 2-(4-bromophenylamino)-4-amino-6-(2,6-dichlorophenyl)-8-methylpyrido[2,3-d]pyrimidin-7(8H)-one, 92.0 mg (0.8 mmol) of L-proline, 76.0 mg (0.4 mmol) of copper iodide, 63.4 mg (0.46 mmol) of potassium carbonate and 437.7 μL (7.82 mmol) of 1-methylpiperazine in 4.6 mL of DMSO was heated in microwave for 16 hours at 80° C. The resulting solution was cooled down and water (400 mL) was added. The resulting precipitate was filtered, washed with water and dried in vacuo over phosphorus pentoxide to afford 140.0 mg (0.27 mmol, 69%) of 4-amino-6-(2,6-dichlorophenyl)-8-methyl-2-(4-(4-methylpiperazin-1-yl)phenylamino)pyrido[2,3-d]pyrimidin-7(8H)-one as a brownish solid.

$^1$H NMR (400 MHz, d$_6$-DMSO) δ 9.21 (br s, 1H), 8.07 (s, 1H), 7.64 (d, J=9.1 Hz, 2H), 7.60-7.55 (m, 2H), 7.43 (dd, J=8.7, 7.5 Hz, 1H), 7.30 (br s, 2H), 6.89 (d, J=9.1 Hz, 2H), 3.58 (s, 3H), 3.12-3.03 (m, 4H), 2.48-2.41 (m, 4H), 2.22 (s, 3H). $^{13}$C NMR (100.6 MHz, d$_6$-DMSO) δ 161.6, 160.5, 159.1, 156.1, 146.4, 135.4, 134.0, 132.3, 130.2, 128.4, 128.0, 120.9, 119.5, 115.7, 91.4, 54.7, 48.8, 45.8, 28.3.

Example 6

4-amino-6-(2,6-dichlorophenyl)-8-methyl-2-(4-(2-morpholinoethylamino)-phenylamino)-pyrido[2,3-d]pyrimidin-7(8H)-one

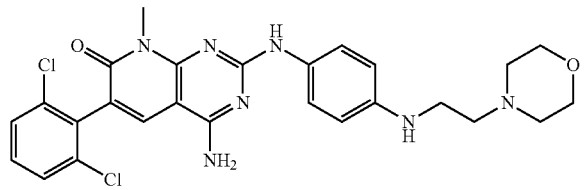 [SMILES: Cn1c(=O)c(-c2c(Cl)cccc2Cl)cc2c(N)nc(Nc3ccc(NCCN4CCOCC4)cc3)nc21]

A mixture of 98.2 mg (0.2 mmol) of 2-(4-bromophenylamino)-4-amino-6-(2,6-dichlorophenyl)-8-methylpyrido[2,3-d]pyrimidin-7(8H)-one, 46.0 mg (0.4 mmol) of L-proline, 38.0 mg (0.2 mmol) of copper iodide, 31.7 mg (0.23 mmol) of potassium carbonate and 513.15 µL (3.91 mmol) of 4-(aminoethyl)morpholine in 2.3 mL of DMSO was heated in microwave for 16 hours at 80° C. The resulting solution was cooled down and water (400 mL) was added. The resulting precipitate was filtered, washed with water and dried in vacuo over phosphorus pentoxide to afford 82.9 mg (0.15 mmol, 77%) of 4-amino-6-(2,6-dichlorophenyl)-8-methyl-2-(4-(2-morpholinoethylamino)-phenylamino)-pyrido[2,3-d]pyrimidin-7(8H)-one as a brownish solid.

$^1$H NMR (400 MHz, d$_6$-DMSO) δ 9.02 (br s, 1H), 8.04 (s, 1H), 7.56 (d, J=8.0 Hz, 2H), 7.47 (d, J=8.0 Hz, 2H), 7.42 (dd, J=8.6, 7.5 Hz, 1H), 7.24 (br s, 2H), 6.56 (d, J=8.8 Hz, 2H), 5.13 (br t, J=5.5 Hz, 1H), 3.59 (t, J=4.6 Hz, 4H), 3.55 (s, 3H), 3.11 (dt, J=6.3, 6.2 Hz, 2H), 2.50 (m, 2H), 2.41 (m, 4H). $^{13}$C NMR (100.6 MHz, d$_6$-DMSO) δ 161.6, 160.5, 159.2, 156.2, 144.5, 135.5, 134.0, 130.2, 129.4, 128.0, 121.9, 119.1, 112.0, 91.2, 66.2, 57.3, 53.4, 40.5, 28.2.

Example 7

4-amino-6-(2,6-dichlorophenyl)-8-methyl-2-(4-(2-morpholinoethoxy)-phenylamino)-pyrido[2,3-d]pyrimidin-7(8H)-one

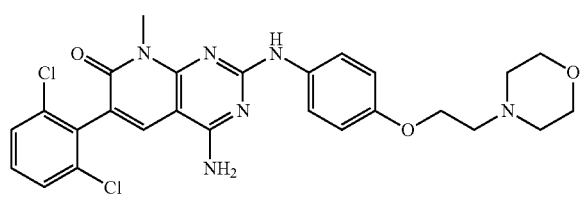 [SMILES: Cn1c(=O)c(-c2c(Cl)cccc2Cl)cc2c(N)nc(Nc3ccc(OCCN4CCOCC4)cc3)nc21]

A mixture of 98.2 mg (0.2 mmol) of 2-(4-bromophenylamino)-4-amino-6-(2,6-dichlorophenyl)-8-methylpyrido[2,3-d]pyrimidin-7(8H)-one, 38.0 mg (0.2 mmol) of copper iodide, 128.0 mg (0.4 mmol) of cesium carbonate and 1.25 mL (8.80 mmol) of 4-(2-hydroxyethyl)morpholine was heated in microwave for 18 hours at 180° C. The solution was cooled down and water (400 mL) was added. The resulting precipitate was filtered, washed with water and dried in vacuo over phosphorus pentoxide. The residue was separated by flash chromatography (silica, CH$_2$Cl$_2$-MeOH; 100:0 to 90:10 in 18 min) to afford 18.9 mg (0.036 mmol, 18%) of 4-amino-6-(2,6-dichloro phenyl)-8-methyl-2-(4-(2-morpholinoethoxy)-phenylamino)-pyrido[2,3-d]pyrimidin-7(8H)-one as a white solid.

$^1$H NMR (400 MHz, d$_6$-DMSO) δ 9.28 (br s, 1H), 8.08 (s, 1H), 7.70 (d, J=9.1 Hz, 2H), 7.60-7.54 (m, 2H), 7.43 (dd, J=8.7, 7.5 Hz, 1H), 7.33 (br s, 2H), 6.89 (d, J=9.1 Hz, 2H), 4.06 (t, J=5.8 Hz, 2H), 3.65-3.53 (m, 7H), 2.68 (t, J=5.8 Hz, 2H), 2.49-2.44 (m, 4H). $^{13}$C NMR (100.6 MHz, d$_6$-DMSO) δ 161.6, 160.5, 159.1, 156.1, 153.6, 135.4, 134.0, 133.5, 130.2, 128.0, 121.3, 119.6, 114.3, 109.6, 91.4, 66.2, 65.5, 57.1, 53.7, 28.3.

Example 8

4-amino-2-(4-aminophenylamino)-6-(2,6-dichlorophenyl)-8-methylpyrido [2,3-d]pyrimidin-7(8H)-one

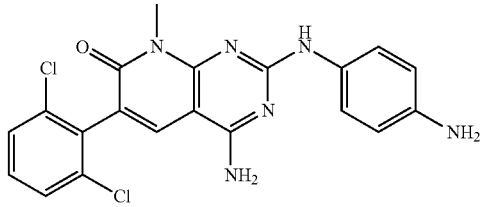 [SMILES: Cn1c(=O)c(-c2c(Cl)cccc2Cl)cc2c(N)nc(Nc3ccc(N)cc3)nc21]

A mixture of 98.2 mg (0.2 mmol) of 2-(4-bromophenylamino)-4-amino-6-(2,6-dichlorophenyl)-8-methylpyrido[2,3-d]pyrimidin-7(8H)-one, 46.0 mg (0.4 mmol) of L-proline, 38.0 mg (0.2 mmol) of copper iodide, 82.7 mg (0.6 mmol) of potassium carbonate and 0.23 mL (3.91 mmol) of ammonia solution 30% in 2.3 mL of DMSO was heated in microwave for 16 hours at 80° C. The solution was cooled down and water (400 mL) was added. The resulting precipitate was filtered, washed with water and dried in vacuo over phosphorus pentoxide. The residue was separated by flash chromatography (silica, CH$_2$Cl$_2$-MeOH; 100:0 to 90:10 in 18 min) to afford 33.6 mg (0.08 mmol, 40%) of 4-amino-2-(4-aminophenylamino)-6-(2,6-dichlorophenyl)-8-methylpyrido[2,3-d]pyrimidin-7(8H)-one as a white solid.

$^1$H NMR (400 MHz, d$_6$-DMSO) δ 8.98 (br s, 1H), 8.04 (s, 1H), 7.60-7.53 (m, 2H), 7.42 (dd, J=8.7, 7.5 Hz, 1H), 7.39 (d, J=8.8 Hz, 2H), 7.24 (br s, 2H), 6.53 (d, J=8.7 Hz, 2H), 4.79 (br s, 2H), 3.54 (s, 3H).

Example 9

4-amino-6-(2,6-dichlorophenyl)-8-methyl-2-(4-(4-methylpiperazin-1-yl)phenylamino)pyrido[2,3-d]pyrimidin-7(8H)-one dimesylate

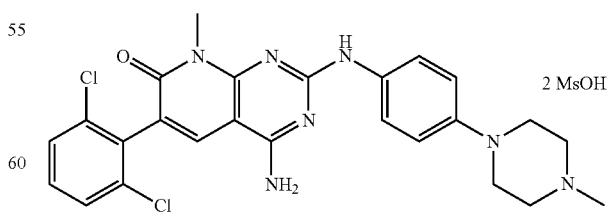

382.8 mg (0.75 mmol) of 4-amino-6-(2,6-dichlorophenyl)-8-methyl-2-(4-(4-methylpiperazin-1-yl)phenylamino)pyrido[2,3-d]pyrimidin-7(8H)-one were firstly dissolved in 50 mL of acetone and then 144.3 mg (1.5 mmol) of methanesulfonic acid were added. The resulting solution was stirred at room temperature for 2 hours and then, cold diethyl ether was added and the resulting precipitated was filtered, washed with cold diethyl ether and dried in vacuo over phosphorus pentoxide to afford 456.7 mg (0.65 mmol, 87%) of 4-amino-6-(2,6-dichlorophenyl)-8-methyl-2-(4-(4-methylpiperazin-1-yl)phenylamino)pyrido[2,3-d]pyrimidin-7(8H)-one dimesylate as a yellowish solid.

$^1$H NMR (400 MHz, $d_6$-DMSO) δ 9.53 (br s, 2H), 9.34 (br s, 1H), 8.09 (s, 1H), 7.70 (d, J=9.1 Hz, 2H), 7.59-7.56 (m, 2H), 7.44 (dd, J=8.7, 7.5 Hz, 1H), 7.43 (br s, 2H), 6.98 (d, J=9.2 Hz, 2H), 3.77 (d, J=13.5 Hz, 2H) 3.59 (s, 3H), 3.52 (d, J=11.9 Hz, 2H) 3.24-3.11 (m, 2H), 2.98-2.84 (m, 5H), 2.34 (s, 6H).

Biological Testing

Kinase Inhibition Profile

The kinase inhibition profile of compounds of formula (I) was evaluated at Proqinase (http://www.proqinase.conn) by measuring residual activity values at a concentration of 10 µM of the test compound in singlicate in front of the following kinases: BTK, LYN, SYK aa1-635 using the following protocol:

The compounds were dissolved to $1\times10^{-03}$ M stock solutions in 100% DMSO. Subsequently, 100 µl of each stock solution were transferred into wells A3-F12 of a microtiter plate ("master plate"). Wells A1-F2 were filled with 100 µl 100% DMSO as controls. 5×10 µl of the master plate were aliquoted into 5 copy plates, which were stored at −20° Celsius until use. For the testing of each group of up to 8 kinases, one copy plate was used.

In the process, 90 µl $H_2O$ were added to each well of a copy plate. To minimize precipitation, the $H_2O$ was added to each well only a few minutes before the transfer of the compound solutions into the assay plates. The plate was shaken thoroughly, resulting in a "compound dilution plate" with a compound concentration of $1\times10^{-04}$ M/10% DMSO. This plate was used for the transfer of 5 µl compound solution into the assay plates. The final volume of the assay was 50 µl. All compounds were tested at $1\times10^{-05}$ M in singlicate. The final DMSO concentration in the reaction cocktails was 1% in all cases. The compound dilution plates were disposed at the end of each working day.

Protein Kinase Assays

A radiometric protein kinase assay ($^{33}$PanQinase® Activity Assay) was used for measuring the kinase activity of the corresponding protein kinases. All kinase assays were performed in 96-well FlashPlates™ from Perkin Elmer (Boston, Mass., USA) in a 50 µl reaction volume. The reaction cocktail was pipetted in 4 steps in the following order:

10 µl of non-radioactive ATP solution (in $H_2O$)
25 µl of assay buffer/[γ-33P]-ATP mixture
5 µl of test sample in 10% DMSO
10 µl of enzyme/substrate mixture The assay for all protein kinases contained 70 mM HEPES-NaOH pH 7.5, 3 mM $MgCl_2$, 3 mM $MnCl_2$, 3 µM Na-orthovanadate, 1.2 mM DTT, ATP (variable amounts, corresponding to the apparent ATP-Km of the respective kinase), [γ-$^{33}$P]-ATP (approx. $8\times10^{05}$ cpm per well), protein kinase (variable amounts), and substrate (variable amounts).

The protein kinase reaction cocktails were incubated at 30° C. for 60 minutes. The reaction was stopped with 50 µl of 2% (v/v) $H_3PO_4$, plates were aspirated and washed two times with 200 µl 0.9% (w/v) NaCl. All assays were performed with a BeckmanCoulter Biomek 2000/SL robotic system. Incorporation of $^{33}$Pi (counting of "cpm") was determined with a microplate scintillation counter (Microbeta, Wallac).

All protein kinase assays were performed with a BeckmanCoulter Core robotic system.

Recombinant Kinases

All protein kinases provided by ProQinase were expressed in Sf9 insect cells or in *E. coli* as recombinant GST-fusion proteins or His-tagged proteins. All kinases were produced from human cDNAs and purified by either GSH-affinity chromatography or immobilized metal. Affinity tags were removed from a number of kinases during purification. The purity of the protein kinases was examined by SDS-PAGE/Coomassie staining, the identity was checked by mass spectroscopy.

Kinases from external vendors (CAR=Carna Biosciences Inc.; INV=Life Technologies (Invitrogen Corporation); MIL=Merck-Millipore (Millipore Corporation)) were expressed, purified and quality-controlled by virtue of the vendors readings.

Evaluation of Raw Data

For each kinase, the median value of the cpm of six wells of column 1 of each assay plate was defined as "low control" (n=6). This value reflects unspecific binding of radioactivity to the plate in the absence of a protein kinase but in the presence of the substrate. Additionally, for each kinase the median value of the cpm of six wells of column 2 of each assay plate was taken as the "high control", i.e. full activity in the absence of any inhibitor (n=6). The difference between high and low control of each enzyme was taken as 100% activity.

As part of the data evaluation the low control of each kinase was subtracted from the high control value as well as from their corresponding "compound values". The residual activity (in %) for each compound well was calculated by using the following formula:

Res. Activity (%)=100×[(signal of compound −low control)/(high control −low control)]

Results

The singlicate residual activity values of the tested compounds at one concentration ($1\times10^{-05}$ M) in singlicate in the required protein kinase assays are given.

Quality Controls

As a parameter for assay quality, the Z″-factor (Zhang et al., *J. Biomol. Screen.* 2: 67-73, 1999) for the low and high controls of each assay plate (n=8) was used. ProQinase's criterion for repetition of an assay plate is a Z″-factor below 0.4 (Iversen et al., *J. Biomol. Screen.* 3: 247-252, 2006). Z'-factors did not drop below 0.51, indicating an excellent assay quality.

Table 2 shows the results obtained for some of the compounds of the present invention.

TABLE 2

| Compound | BTK | LYN | SYK aa1-635 |
|---|---|---|---|
| Example 5 | 3 | −1 | 9 |
| Example 6 | 10 | 0 | 31 |
| Example 7 | 16 | 0 | 44 |

Assays in Non-Hodgkin's Lymphomas Cell Lines and on the Activity of BCR Kinases

Methods

Cell culture: cell lines were grown in suitable culture media at 37° C. in a humidified atmosphere containing 5% $CO_2$. The following MCL cell lines were used in the assays: Rec-1, HBL-2, UPN-1, Jeko-1, JVM-2, Maver-1, Mino, Granta-519, and Z-138. The following CLL cell lines were used in the assays: MEC-2, JVM-13, and MEC-1. The following FL cell lines were used in the assays: DoHH-2, WSU-NHL, WSU-FSCCL, and SC-1. The following DLBCL cell lines were used in the assays: OCI-LY8, SUDHL-8, U-2932, and SUDHL-16. The following media were used for the indicated cell lines: RPMI 1640+10% foetal bovine serum (FBS) for Rec-1, HBL-2, UPN-1, JVM-2, MAVER, Z138, Mino, JVM-13, WSU-NHL, WSU-FSCCL, DOHH2, SC-1 and U2932; RPMI 1640+20% FBS for Jeko-1, SUDHL-8 and SUDHL-16; DMEM+10% FBS for Granta-519; IMDM+10% FBS for MEC-1 and MEC-2; IMDM+20% FBS for OCI-LY8.

Analysis of the growth inhibition is carried out using the MTT (Thiazolyl Blue Tetrazolium Bromide) proliferation assay: cells grown in exponential phase were seeded in 96 well plates at $0.5 \times 10^6$ cell/ml and treated with 4-amino-6-(2,6-dichlorophenyl)-8-methyl-2-(4-(4-methylpiperazin-1-yl)phenylamino)pyrido[2,3-d]pyrimidin-7(8H)-one (Example 5) at the doses of 0.5, 1.5, 10, 20, 50 and 100 μM. After 24 h or 48 h, MTT reagent was added to each well, incubated for 2 h and plates were then read in a Synergy-HT Multi-Mode Microplate Reader (Biotek). The $GI_{50}$ (concentration of drug required to reduce cell growth by 50%) was calculated from the cytotoxic values obtained by incubating cells with the indicated doses of the drug using GraphPad Prism software version 4.0.

Analysis of B-Cell Receptor (BCR) activation signaling molecules by Western Blot and flow cytometry. Total protein extracts in 1% Triton X-100 plus protease and phosphatase inhibitors were made from cells treated with a range of doses of the indicated compound (0.1, 1, 5 and 10 μM). These cells lysates were resolved by standard SDS-PAGE (sodium dodecyl sulfate polyacrylamide gel electrophoresis), transferred to PVDF (polyvinylidene difluoride) membranes and incubated overnight with the indicated primary antibodies (pSyk, pLyn and β-actin) followed by species-matched secondary horseradish peroxidase (HRP)-labelled antibodies. Chemiluminiscence was developed adding ECL (enhanced chemilumiscence) reagent and signal was captured in a LAS4000 device using Image Gauge software (Fujifilm). Intracellular amount of PhosphoY223-Btk was determined by inmunostaining with an anti-phosphoY223-Btk-PE antibody (clone N35-86), using IgG1 K isotype-PE as negative control (BD Biosciences). After the different treatments, cells ($5 \times 10^5$) were fixed in 4% paraformaldehyde in PBS (15 min, 4° C.), permeabilized with cold methanol (10 min, −20° C.), washed with PBS containing 1% BSA and incubated with the indicated antibodies at room temperature for 15 min. Finally, cells were washed with PBS containing 1% BSA, resuspended in 500 μl PBS and analyzed by flow cytometry in an Attune acoustic focusing cytometer (Life Technologies). The Mean Fluorescence Ratio (MFIR) between the mean fluorescence intensity of Btk-PE signal and isotypic control was then calculated for both untreated and treated conditions. These MFIR were then referred to the untreated control (r).

Results

Antitumoral activity of a compound of Formula (I) in non-Hodgkin's lymphomas cell lines involving the inhibition of B-Cell receptor (BCR)-related kinases: the activity of a compound of Formula I, namely 4-amino-6-(2,6-dichlorophenyl)-8-methyl-2-(4-(4-methylpiperazin-1-yl)phenylamino)pyrido[2,3-d]pyrimidin-7(8H)-one (Example 5) against a panel of 20 NHLs cell lines was assessed by MTT assay. Cells were exposed for 24 h or 48 h to increasing doses of the compound and $GI_{50}$ values were calculated and represented on FIG. 1. The compound showed comparable antiproliferative activity at 24 h and 48 h in the tested cell lines, with $GI_{50}$ ranging from 1.3 to 6.9 μM (mean=4.3) at 24 h, and from 1.4 to 7.2 μM (mean=3.6) at 48 h. Table 3 shows the detailed range of $GI_{50}$ values for each pathology.

TABLE 3

Mean $GI_{50}$ values of 4-amino-6-(2,6-dichlorophenyl)-8-methyl-2-(4-(4-methylpiperazin-1-yl)phenylamino)pyrido[2,3-d]pyrimidin-7(8H)-one (Example 5) in MCL, CLL, FL and DLBCL cell lines at 24 and 48 hours.

|  | MCL (n = 9 cell lines) | CLL (n = 3 cell lines) | FL (n = 4 cell lines) | DLBCL (n = 4 cell lines) |
| --- | --- | --- | --- | --- |
| Mean $GI_{50}$ at 24 h (μM) | 3.6 (range: 1.3-5.9) | 5.9 (range: 5.3-6.8) | 3.7 (range: 2.6-4.9) | 5.4 (range: 4.3-6.9) |
| Mean $GI_{50}$ at 48 h (μM) | 3.0 (range: 2.2-3.6) | 4.9 (range: 4.5-5.5) | 2.7 (range: 1.4-4.4) | 5.0 (range: 3.8-7.2) |

Figure 2:
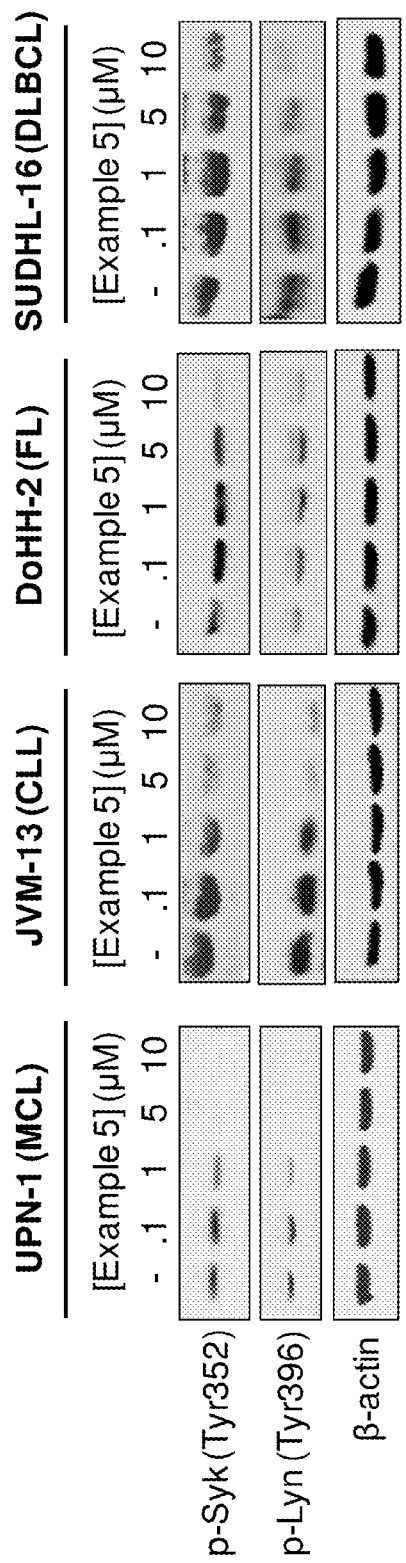
FIG. 2 shows the dose-effect of 4-amino-6-(2,6-dichlorophenyl)-8-methyl-2-(4-(4-methylpiperazin-1yl)phenylamino)pyrido[2,3-d]pyrimidin-7(8H)-one) on the phosphorylation status of the B-Cell receptor (BCR)-related kinases Syk and Lyn in UPN-1 (an MCL cell line), JVM-13 (a CLL cell line), DoHH-2 (a FL cell line) and SUDHL-16 (a DLBCL cell line) cells after 6 h of treatment.
Figure 3:
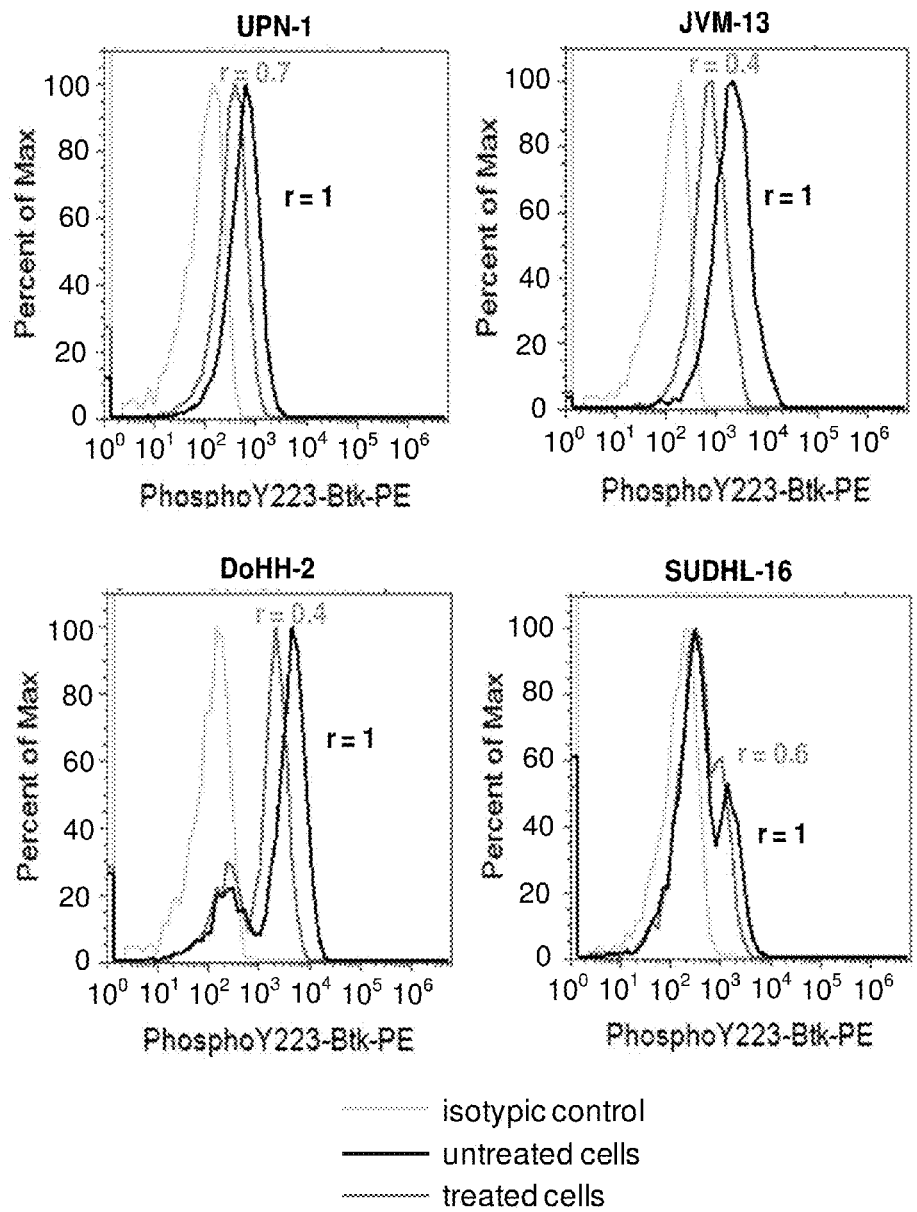
FIG. 3 shows the effect of a single dose (5 µM) of 4-amino-6-(2,6-dichlorophenyl)-8-methyl-2-(4-(4-methylpiperazin-1yl)phenylamino)pyrido[2,3-d]pyrimidin-7(8H)-one) on the phosphorylation status of the BCR-related kinase Btk in UPN-1 (an MCL cell line), JVM-13 (a CLL cell line), DoHH-2 (a FL cell line) and SUDHL-16 (a DLBCL cell line) cells after 6 h of treatment. r values indicate the relative mean fluorescence intensity between Btk-PE signal and isotypic control, as assessed by flow cytometry analysis of both untreated (black lines) and treated (grey lines) cells. Untreated control cells were used as calibrators (r=1).

To further assess the inhibitory effect of 4-amino-6-(2,6-dichlorophenyl)-8-methyl-2-(4-(4-methylpiperazin-1-yl)phenylamino)pyrido[2,3-d]pyrimidin-7(8H)-one (Example 5) on the activity of BCR kinases, a set of 4 cell lines representative of each entity was exposed for 6 h to increased doses of 4-amino-6-(2,6-dichlorophenyl)-8-methyl-2-(4-(4-methylpiperazin-1-yl)phenylamino)pyrido[2,3-d]pyrimidin-7(8H)-one (Example 5) and cell contents in phospho-Syk and phospho-Lyn were analysed by SDS-PAGE and western blotting with specific antibodies, using β-actin as a loading control. FIG. 2 shows that the compound inhibited Syk and Lyn phosphorylation as soon as 6 h of treatment in the 4 cell lines analyzed, and in a dose-dependent fashion. Off note, phosphorylation inhibition by 4-amino-6-(2,6-dichlorophenyl)-8-methyl-2-(4-(4-methylpiperazin-1-yl)phenylamino)pyrido[2,3-d]pyrimidin-7(8H)-one (Example 5) was already detectable at 1 μM dose, significantly enhanced at 5 μM and almost completely achieved at 10 μM. For the evaluation of phospho-Btk protein levels, cell lines were treated as above with a 5 μM dose of the compound and stained with an anti-phospho-Btk phycoerythin(PE)-labeled antibody followed by flow cytometry analysis. FIG. 3 shows that the downregulation of phospho-Btk was variable but constant among the cell lines exposed to the compound, ranging from 30% (in UPN-1 cells) to 60% (in JVM-13 and DoHH-2 cells), based on the decrease of the mean fluorescence intensity ratios.

Altogether, these results indicate that a compound of Formula (I) exerts a dose-dependent antitumoral activity in MCL, CLL, FL and DLBCL cells, in the micromolar range, and that this effect is related to the inhibition of the phosphorylation of BCR-related kinases.

All references cited in the example section are incorporated by reference in their entirety.

The invention claimed is:
1. A compound of formula (I):

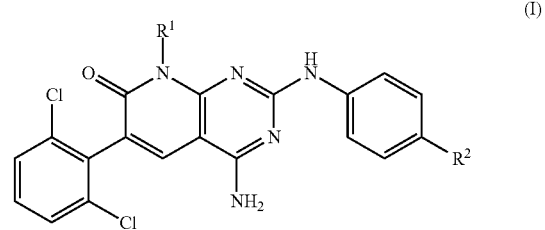

wherein

R$^1$ is selected from the group consisting of

H;

C$_1$-C$_6$ alkyl optionally substituted with one, two or three substituents independently selected from the group consisting of hydroxy; C$_1$-C$_6$ alkoxy, C$_1$-C$_6$ alkylthio, di(C$_1$-C$_6$ alkyl)amino, C$_1$-C$_6$ alkoxycarbonyl, cyano, and F;

C$_3$-C$_8$ cycloalkyl optionally substituted with one, two or three substituents independently selected from the group consisting of hydroxy; C$_1$-C$_6$ alkoxy, C$_1$-C$_6$ alkylthio, C$_1$-C$_6$ alkoxycarbonyl, di(C$_1$-C$_6$ alkyl)amino, cyano, and F;

C$_3$-C$_8$ cycloalkyl-C$_1$-C$_3$ alkylene, wherein the cycloalkyl is optionally substituted with one, two or three substituents independently selected from the group consisting of hydroxy; C$_1$-C$_6$ alkoxy, C$_1$-C$_6$ alkylthio, C$_1$-C$_6$ alkoxycarbonyl, di(C$_1$-C$_6$ alkyl)amino, cyano, and F;

C$_6$-C$_{14}$ aryl optionally substituted with one, two or three substituents independently selected from the group consisting of C$_1$-C$_6$ alkyl, C$_1$-C$_6$ alkoxy, C$_1$-C$_6$ alkylthio, F, Cl, Br, C$_1$-C$_6$ alkoxycarbonyl, C$_1$-C$_6$ alkylcarbonyl, C$_3$-C$_8$ cycloalkylcarbonyl, C$_1$-C$_6$ alkylcarbonyloxy, amino, C$_1$-C$_6$ alkylamino, di(C$_1$-C$_6$ alkyl)amino, di(C$_1$-C$_6$ alkyl)aminocarbonyl, cyano, hydroxyl, hydroxy-C$_1$-C$_6$ alkyleneoxy, carboxy, C$_1$-C$_6$ alkylcarbonyloxy, C$_1$-C$_6$ alkylsulfonyl, C$_1$-C$_6$ alkylsulfinyl, di(C$_1$-C$_6$ alkyl)aminocarbonyloxy, di(C$_1$-C$_6$ alkyl)amino-C$_1$-C$_6$ alkyleneoxy, C$_1$-C$_6$ alkoxycarbonyl, and C$_1$-C$_6$ alkoxy-C$_1$-C$_6$ alkyleneoxy;

C$_6$-C$_{14}$ aryl-C$_1$-C$_3$ alkylene, wherein the aryl is optionally substituted with one, two or three substituents independently selected from the group consisting of C$_1$-C$_6$ alkyl, C$_1$-C$_6$ alkoxy, C$_1$-C$_6$ alkylthio, F, Cl, Br, C$_1$-C$_6$ alkoxycarbonyl, C$_1$-C$_6$ alkylcarbonyl, C$_3$-C$_8$ cycloalkylcarbonyl, C$_1$-C$_6$ alkylcarbonyloxy, amino, C$_1$-C$_6$ alkylamino, di(C$_1$-C$_6$ alkyl)amino, di(C$_1$-C$_6$ alkyl)aminocarbonyl, cyano, hydroxyl, hydroxy-C$_1$-C$_6$ alkyleneoxy, carboxy, C$_1$-C$_6$ alkylcarbonyloxy, C$_1$-C$_6$ alkylsulfonyl, C$_1$-C$_6$ alkylsulfinyl, di(C$_1$-C$_6$ alkyl)aminocarbonyloxy, di(C$_1$-C$_6$ alkyl)amino-C$_1$-C$_6$ alkyleneoxy, C$_1$-C$_6$ alkoxycarbonyl, and C$_1$-C$_6$ alkoxy-C$_1$-C$_6$ alkyleneoxy;

3- to 8-membered monocyclic or 5- to 12-membered bicyclic saturated or partially saturated heterocyclyl which contains from 1 to 4 heteroatoms in the ring independently selected from the group consisting of N, O, and S, and wherein the heterocyclyl is optionally substituted with one, two or three substituents independently selected from the group consisting of hydroxy; C$_1$-C$_6$ alkoxy, C$_1$-C$_6$ alkylthio, C$_1$-C$_6$ alkoxycarbonyl, di(C$_1$-C$_6$ alkyl)amino, cyano, and F;

heterocyclyl-C$_1$-C$_3$ alkylene, wherein the heterocyclyl is a 3- to 8-membered monocyclic or 5- to 12-membered bicyclic saturated or partially saturated ring system which contains from 1 to 4 heteroatoms in the ring independently selected from the group consisting of N, O, and S as defined above, and wherein the heterocyclyl-C$_1$-C$_3$ alkyl is optionally substituted at the heterocyclyl moiety with one, two or three substituents independently selected from the group consisting of hydroxy; C$_1$-C$_6$ alkoxy, C$_1$-C$_6$ alkylthio, C$_1$-C$_6$ alkoxycarbonyl, di(C$_1$-C$_6$ alkyl)amino, cyano, and F;

5- to 6-membered monocyclic or 8- to 14-membered bicyclic heteroaryl which contains from 1 to 4 heteroatoms in the ring system independently selected from the group consisting of N, O, and S, and wherein the heteroaryl is optionally substituted with one, two or three substituents independently selected from the group consisting of C$_1$-C$_6$ alkyl, C$_1$-C$_6$ alkoxy, C$_1$-C$_6$ alkylthio, F, Cl, Br, C$_1$-C$_6$ alkoxycarbonyl, C$_1$-C$_6$ alkylcarbonyl, C$_3$-C$_8$ cycloalkylcarbonyl, C$_1$-C$_6$ alkylcarbonyloxy, amino, C$_1$-C$_6$ alkylamino, di(C$_1$-C$_6$ alkyl)amino, di(C$_1$-C$_6$ alkyl)aminocarbonyl, cyano, hydroxyl, hydroxy-C$_1$-C$_6$ alkyleneoxy, carboxy, C$_1$-C$_6$ alkylcarbonyloxy, C$_1$-C$_6$ alkylsulfonyl, C$_1$-C$_6$ alkylsulfinyl, di(C$_1$-C$_6$ alkyl)aminocarbonyloxy, di(C$_1$-C$_6$ alkyl)amino-C$_1$-C$_6$ alkyleneoxy, C$_1$-C$_6$ alkoxycarbonyl, and C$_1$-C$_6$ alkoxy-C$_1$-C$_6$ alkyleneoxy; and heteroaryl-C$_1$-C$_3$ alkylene, wherein the heteroaryl is a 5- to 6-membered monocyclic or 8- to 14-membered bicyclic ring system which contains from 1 to 4 heteroatoms in the ring independently selected from the group consisting of N, O, and S, and wherein the heteroaryl is optionally substituted with one, two or three substituents independently selected from the group consisting of C$_1$-C$_6$ alkyl, C$_1$-C$_6$ alkoxy, C$_1$-C$_6$ alkylthio, F, Cl, Br, C$_1$-C$_6$ alkoxycarbonyl, C$_1$-C$_6$ alkylcarbonyl, C$_3$-C$_8$ cycloalkylcarbonyl, C$_1$-C$_6$ alkylcarbonyloxy, amino, C$_1$-C$_6$ alkylamino, di(C$_1$-C$_6$ alkyl)amino, di(C$_1$-C$_6$ alkyl)aminocarbonyl, cyano, hydroxyl, hydroxy-C$_1$-C$_6$ alkyleneoxy, carboxy, C$_1$-C$_6$ alkylcarbonyloxy, C$_1$-C$_6$ alkylsulfonyl, C$_1$-C$_6$ alkylsulfinyl, di(C$_1$-C$_6$ alkyl)aminocarbonyloxy, di(C$_1$-C$_6$ alkyl)amino-C$_1$-C$_6$ alkyleneoxy, C$_1$-C$_6$ alkoxycarbonyl, and C$_1$-C$_6$ alkoxy-C$_1$-C$_6$ alkyleneoxy;

R$^2$ is selected from the group consisting of

H; Cl, Br, I; —NR$^3$R$^4$; and —OR$^5$;

where R$^3$ is H and R$^4$ is selected from the group consisting of H and —C$_1$-C$_6$ alkylene-NR$^6$R$^7$;

or R$^3$ and R$^4$ together with the nitrogen atom to which they are attached form a saturated or partially saturated 3- to 8-membered monocyclic or 5- to 12-membered bicyclic heterocyclyl which contains from 1 to 4 heteroatoms in the ring system independently selected from the group consisting of N, O, and S, and which is optionally substituted with one, two or three substituents independently selected from the group consisting of C$_1$-C$_6$ alkoxy, C$_1$-C$_6$ alkylthio, C$_1$-C$_6$ alkoxycarbonyl, di(C$_1$-C$_6$ alkyl)amino, cyano, and F;

R$^5$ is —C$_1$-C$_6$ alkylene-NR$^6$R$^7$;

R$^6$ is selected from the group consisting of H and C$_1$-C$_6$ alkyl;

R$^7$ is C$_1$-C$_6$ alkyl;

or R$^6$ and R$^7$ together with the nitrogen atom to which they are attached form a 3- to 8-membered saturated or partially saturated monocyclic heterocyclyl which contains form 1 to 4 heteroatoms in the ring system independently selected from the group consisting of N, O, and S, and which is optionally substituted with one, two or three substituents independently selected from the group consisting of C$_1$-C$_6$ alkoxy, C$_1$-C$_6$ alkylthio, C$_1$-C$_6$ alkoxycarbonyl, di(C$_1$-C$_6$ alkyl)amino, cyano, and F;

or a stereoisomer or a pharmaceutically acceptable salt thereof.

2. The compound of formula (I) according to claim 1, wherein
$R^1$ is selected from the group consisting of H; $C_1$-$C_6$ alkyl optionally substituted with one, two or three substituents independently selected from the group consisting of hydroxyl, $C_1$-$C_6$ alkoxy, $C_1$-$C_6$ alkylthio, di($C_1$-$C_6$ alkyl)amino, $C_1$-$C_6$ alkoxycarbonyl, cyano, and F; $C_6$-$C_{10}$ aryl-$C_1$-$C_3$ alkylene wherein the aryl moiety is optionally substituted with one, two or three substituents independently selected from the group consisting of $C_1$-$C_6$ alkyl, $C_1$-$C_6$ alkoxy, $C_1$-$C_6$ alkylthio, F, Cl, Br, $C_1$-$C_6$ alkoxycarbonyl, $C_1$-$C_6$ alkylcarbonyl, $C_3$-$C_8$ cycloalkylcarbonyl, $C_1$-$C_6$ alkylcarbonyloxy, amino, $C_1$-$C_6$ alkylamino, di($C_1$-$C_6$ alkyl)amino, di($C_1$-$C_6$ alkyl)aminocarbonyl, cyano, hydroxyl, hydroxy-$C_1$-$C_6$ alkyleneoxy, carboxy, $C_1$-$C_6$ alkylcarbonyloxy, $C_1$-$C_6$ alkylsulfonyl, $C_1$-$C_6$ alkylsulfinyl, di($C_1$-$C_6$ alkyl)aminocarbonyloxy, di($C_1$-$C_6$ alkyl)amino-$C_1$-$C_6$ alkyleneoxy, $C_1$-$C_6$ alkoxycarbonyl, and $C_1$-$C_6$ alkoxy-$C_1$-$C_6$ alkyleneoxy.

3. The compound of formula (I) according to claim 1, wherein $R^1$ is selected from the group consisting of H, unsubstituted $C_1$-$C_3$ alkyl, and unsubstituted $C_6$-$C_{10}$ aryl-$C_1$-$C_3$ alkylene.

4. The compound of formula (I) according to claim 3, wherein $R^1$ is selected from the group consisting of H, methyl, and benzyl.

5. The compound of formula (I) according to claim 1, wherein $R^2$ is selected from the group consisting of H; Br; —$NR^3R^4$; and —$OR^5$;
wherein $R^3$ is H; $R^4$ is selected from the group consisting of H and —$C_1$-$C_6$ alkylene-$NR^6R^7$; or $R^3$ and $R^4$ together with the nitrogen atom to which they are attached form a saturated 5- to 7-membered monocyclic heterocyclyl which contains from 1 to 2 heteroatoms in the ring system independently selected from the group consisting of N, O, and S, and which is optionally substituted with one, two or three substituents independently selected from the group consisting of $C_1$-$C_6$ alkoxy, $C_1$-$C_6$ alkylthio, $C_1$-$C_6$ alkoxycarbonyl, di($C_1$-$C_6$ alkyl)amino, cyano, and F; $R^5$ is —$C_1$-$C_6$ alkylene-$NR^6R^7$; and wherein $R^6$ and $R^7$ together with the nitrogen atom to which they are attached form a 5- to 7-membered saturated monocyclic heterocyclyl which contains from 1 to 2 heteroatoms in the ring system selected from the group consisting of N and O, and which is optionally substituted with one, two or three substituents independently selected from the group consisting of $C_1$-$C_6$ alkoxy, $C_1$-$C_6$ alkylthio, $C_1$-$C_6$ alkoxycarbonyl, di($C_1$-$C_6$ alkyl)amino, cyano, and F.

6. The compound of formula (I) according to claim 5, wherein
$R^2$ is selected from the group consisting of H; Br; $NR^3R^4$; and —$OR^5$; wherein $R^3$ is H; $R^4$ is selected from the group consisting of H and —$C_1$-$C_3$ alkylene-$NR^6R^7$; or $R^3$ and $R^4$ together with the nitrogen atom to which they are attached form a heterocyclyl selected from the group consisting of morpholinyl, piperidinyl optionally substituted with $C_1$-$C_3$ alkyl, piperazinyl optionally substituted with $C_1$-$C_3$ alkyl, and pyrrolidinyl; $R^5$ is —$C_1$-$C_3$ alkylene-$NR^6R^7$; and $R^6$ and $R^7$ together with the nitrogen atom to which they are attached form a heterocyclyl selected from the group consisting of morpholinyl, piperidinyl optionally substituted with $C_1$-$C_3$ alkyl, piperazinyl optionally substituted with $C_1$-$C_3$ alkyl, and pyrrolidinyl.

7. The compound of formula (I) according to claim 6, wherein $R^2$ is selected from the group consisting of —$NR^3R^4$ and —$OR^5$; wherein $R^3$ is H; $R^4$ is —$C_1$-$C_3$ alkylene-$NR^6R^7$; or $R^3$ and $R^4$ together with the nitrogen atom to which they are attached form a piperazinyl optionally substituted with $C_1$-$C_3$ alkyl; $R^5$ is —$C_1$-$C_3$ alkylene-$NR^6R^7$; and $R^6$ and $R^7$ together with the nitrogen atom to which they are attached form a morpholinyl.

8. The compound of formula (I) according to claim 1 which is selected from the group consisting of:
4-amino-6-(2,6-dichlorophenyl)-2-(phenylamino)pyrido[2,3-d]pyrimidin-7(8H)-one;
4-amino-6-(2,6-dichlorophenyl)-8-methyl-2-(phenylamino)pyrido[2,3-d]pyrimidin-7(8H)-one;
4-amino-8-benzyl-6-(2,6-dichlorophenyl)-2-(phenylamino)pyrido[2,3-d]pyrimidin-7(8H)-one;
4-amino-2-(4-bromophenylamino)-6-(2,6-dichlorophenyl)-8-methylpyrido[2,3-d]pyrimidin-7(8H)-one;
4-amino-6-(2,6-dichlorophenyl)-8-methyl-2-(4-(4-methylpiperazin-1-yl)phenylamino)pyrido[2,3-d]pyrimidin-7(8H)-one;
4-amino-6-(2,6-dichlorophenyl)-8-methyl-2-(4-(2-morpholinoethylamino)-phenylamino)pyrido[2,3-d]pyrimidin-7(8H)-one;
4-amino-6-(2,6-dichlorophenyl)-8-methyl-2-(4-(2-morpholinoethoxy)-phenylamino)pyrido[2,3-d]pyrimidin-7(8H)-one; and
4-amino-2-(4-aminophenylamino)-6-(2,6-dichlorophenyl)-8-methylpyrido[2,3-d]pyrimidin-7(8H)-one;
or a stereoisomer or pharmaceutically acceptable salt thereof.

9. A pharmaceutical composition which comprises a compound of formula (I) as defined in claim 1 or a stereoisomer or a pharmaceutically acceptable salt thereof, and one or more pharmaceutically acceptable excipients.

* * * * *

UNITED STATES PATENT AND TRADEMARK OFFICE
CERTIFICATE OF CORRECTION

PATENT NO. : 9,630,962 B2
APPLICATION NO. : 14/897590
DATED : April 25, 2017
INVENTOR(S) : Jose Ignacio Borrell Bilbao et al.

It is certified that error appears in the above-identified patent and that said Letters Patent is hereby corrected as shown below:

On the Title Page

Under (73) Assignees: "Hospital Clinic de Barcelona" should be --Hospital Clínic de Barcelona--.

In the Specification

Column 3, Line 14: "Péréz-Galán P," should be --Pérez-Galán P,--.

Column 4, Lines 64-65: "(4-methyl piperazin1yl)" should be --(4-methylpiperazin-1yl)--.

Column 18, Line 64: "Br, CI," should be --Br, Cl,--.

Column 21, Line 52: "constants (0.1)" should be --constants (J)--.

Column 21, Line 61: "with RediSep' silica" should be --with Redi*Sep*® silica--.

Column 27, Line 18: "(http://www.proqinase.conn)" should be --(http://www.proqinase.com)--.

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*